US010844360B2

(12) United States Patent
Gjermansen et al.

(10) Patent No.: US 10,844,360 B2
(45) Date of Patent: Nov. 24, 2020

(54) POLYPEPTIDES

(71) Applicant: Novozymes A/S, Bagsvaerd (DK)

(72) Inventors: Morten Gjermansen, Greve (DK);
Klaus Gori, Dyssegaard (DK); Henrik Marcus Geertz-Hansen, Copenhagen (DK); Jesper Salomon, Holte (DK); Mary Ann Stringer, Soborg (DK); Thomas Holberg Blicher, Copenhagen (DK); Nikolaj Spodsberg, Holte (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/737,169

(22) PCT Filed: Oct. 7, 2016

(86) PCT No.: PCT/EP2016/074115
§ 371 (c)(1),
(2) Date: Dec. 15, 2017

(87) PCT Pub. No.: WO2017/060505
PCT Pub. Date: Apr. 13, 2017

(65) Prior Publication Data
US 2018/0187175 A1    Jul. 5, 2018

(30) Foreign Application Priority Data

Oct. 7, 2015  (DK) .................................. 2015 00617

(51) Int. Cl.
*C12N 9/22* (2006.01)
*C11D 3/386* (2006.01)
*C11D 3/20* (2006.01)
*C11D 3/22* (2006.01)
*C11D 3/37* (2006.01)
*C11D 11/00* (2006.01)

(52) U.S. Cl.
CPC .............. *C12N 9/22* (2013.01); *C11D 3/2065* (2013.01); *C11D 3/22* (2013.01); *C11D 3/3707* (2013.01); *C11D 3/38627* (2013.01); *C11D 3/38636* (2013.01); *C11D 3/38681* (2013.01); *C11D 11/0017* (2013.01); *C12Y 301/21* (2013.01); *C12Y 301/21001* (2013.01)

(58) Field of Classification Search
None
See application file for complete search history.

(56) References Cited

U.S. PATENT DOCUMENTS 6,340,566 B1   1/2002  McCutchen-Maloney
6,365,355 B1   4/2002  McCutchen-Maloney
2012/0060300 A1  3/2012  Kim et al.

FOREIGN PATENT DOCUMENTS

| EP | 2617824 A1 | 7/2013 |
|----|-----------|--------|
| WO | 01/986214 A1 | 12/2001 |
| WO | 2009/107091 A2 | 9/2009 |
| WO | 2009/111258 A2 | 9/2009 |
| WO | 2011/015327 A1 | 2/2011 |
| WO | 2011/098579 A1 | 8/2011 |
| WO | 2014/087011 A1 | 6/2014 |
| WO | 2015/181286 A1 | 12/2015 |
| WO | 2017/162836 A1 | 9/2017 |
| WO | 2018/011276 A1 | 1/2018 |

OTHER PUBLICATIONS

Merriam-Webster Dictionary definition of "granule", obtained from www.merriam-webster.com on Jan. 22, 2020, 1 page. (Year: 2020).*
Anonymous, NCBI Accession No. WP_004251670 (2013).
Anonymous, UniParc Accession No. UPI0003A82032 (2013).
Anonymous, NCBI Accession No. WP_029440352 (2014).
Anonymous, NCBI Accession No. WP_034664156 (2014).
Anonymous, NCBI Accession No. WP_0275722554 (2014).
Anonymous, NCBI Accession No. WP_027924635 (2014).
Anonymous, NCBI Accession No. WP_028551502 (2014).
Anonymous, NCBI Accession No. WP_041089515 (2015).
Anonymous, NCBI Accession No. WP_047969415 (2015).
Anonymous, NCBI Accession No. WP_039304398 (2015).
Anonymous, NCBI Accession No. WP_045521827 (2015).
Anonymous, NCBI Accession No. WP_051450038 (2015).
Anonymous, NCBI Accession No. WP_030603405.1 (2016).
Anonymous, NCBI Accession No. WP_031424130 (2016).
Anonymous, NCBI Accession No. WP_034817012 (2016).
Baumgarten et al., GenBank Accession No. KXJ07836 (2015).
Chancey et al., UniProt Accession No. J1GW18 (2012).
Chen et al., UniProt Accession No. S3D1S1 (2013).
Chen et al., UniProt Accession No. S3DWR8 (2013).
Coleman et al., EBI Accession No. C7YPZ7 (2009).
Connell et al., UniProt Accession No. H1V7F8 (2012).
Daniel, UniProt Accession No. A0A0E4HDQ4 (2015).
Feldgarden et al., GenBank Accession No. EJR08198 (2012).
Franco et al., EMBL Accession No. A0A0L1HKH6 (2015).
Gao et al., PLoS Genetics, vol. 7, Issue 1, No. E1001264 (2011).
Gori et al., IP.com No. IPCOM000237363D (2014).
Gostin et al., EBI Accession No. A0A074YFK3 (2014).
Greiner-Stoffele et al., EBI Accession No. JA286954 (2011).
Hymes et al., Journal of Infectious Disease, vol. 207, No. 10, pp. 1491-1497 (2013).
Lian et al., GenBank Accession No. AFK65439 (2013).
Liu et al., GenBank Accession No. KMY52255 (2015).
Ma et al., EBI Accession No. H6NAU2 (2012).
Marincowitz et al, Genbank accession No. EU552123 (2008).
Martin et al., Trends in Biochemical Sciences, vol. 21, No. 8, pp. 283-285 (1996).

(Continued)

*Primary Examiner* — David Steadman
(74) *Attorney, Agent, or Firm* — Kristin McNamara

(57) ABSTRACT

The present invention relates to polypeptides, nucleotides encoding the polypeptide, as well as methods of producing the polypeptides. The present invention also relates to detergent composition comprising polypeptides, a laundering method and the use of polypeptides.

21 Claims, No Drawings

Specification includes a Sequence Listing.

(56) References Cited

OTHER PUBLICATIONS

McCutchen-Maloney, EBI Accession No. AAE89259 (2002).
McCutchen-Maloney, EBI Accession No. AAM56188 (2002).
Murphy, EMBL Accession No. A0A0T9L4U8 (2015).
Neafsey et al., EMBL Accession No. A0A0J8TUN1 (2010).
Nijland et al., PLoS One, vol. 5, Issue 12, No. e15668 (2010).
Osei et al., EMBL Accession No. A0A0P8G0A5 (2015).
Sharma et al., EMBL Accession No. A0A0F5R1U3 (2015).
Shields et al., PLoS One, vol. 8, Issue 2, No. e55339 (2013).
Tran et al., EMBL Accession No. A0A0K6K3H5 (2015).
Vandeputte et al., UniProt Accession No. A0A084G9H5 (2014).
Wang et al., EMBL Accession No. A0A0C5AGR7 (2015).
Wang et al., GenBank Accession No. AJK28734 (2015).
Yoon et al., EMBL Accession No. A0A084H293 (2005).
Zhu et al., EMBL Accession No. A0A0F7TT23 (2014).
Anonymous, NCBI Accession No. WP_025722554 (2014).
Anonymous, NCBI Accession No. WP_035510436 (2016).
Birren et al., EBI Accession No. Q5ARC4 (2005).
Birren et al., EBI Accession No. Q2GRF9 (2006).
Cuomo et al., EBI Accession No. U7Q814 (2014).
Cuomo et al., EBI Accession No. A0A0D2ITS4 (2015).
Fedorova et al., EBI Accession No. A1D7D1 (2007).
Gibson, EBI Accession No. A0A0A1V6B7 (2015).
Hane et al., EBI Accession No. Q0U4Q1 (2006).
Klosterman et al., EBI Accession No. G2WSK6 (2011).
Kwak et al., EMBL Accession No. A0A086GGG3 (2014).
Lawrence et al., EBI Accession No. A0A0G2FAG3 (2015).
Ohm et al., EBI Accession No. M2N7N4 (2013).
Ohm et al., EBI Accession No. M2S5C4 (2013).
Pei et al., EBI Accession No. A2QFZ2 (2007).
Traeger et al., EBI Accession No. U4LM18 (2013).
Wang et al., EBI Accession No. W3WUK5 (2014).
Ngo et al, 1994, The Protein Folding Problem and Tertiary Structure Prediction, vol. 433 ABD pp. 492-495.

* cited by examiner

SEQUENCE LISTING

<160> NUMBER OF SEQ ID NOS: 21

<210> SEQ ID NO 1
<211> LENGTH: 122
<212> TYPE: PRT
<213> ORGANISM: Paenibacillus sp-62212

```
<400> SEQUENCE: 1

Glu Thr Glu Pro Thr Thr Gln Gln Ala Ala Gly Ser Thr Ser Ala Glu
1               5                   10                  15

Thr Ile Thr Leu Tyr Phe Pro Gln Asp Arg Phe Pro Glu Thr Gly Lys
            20                  25                  30

His Ile Lys Asn Ala Ile Ala Ser Gly Glu Ser Ser Ile Cys Thr Ile
        35                  40                  45

Asp Arg Lys Gln Ala Glu Glu Asn Arg Lys His Ser Leu Lys Gly Ile
    50                  55                  60

Pro Thr Lys Lys Gly Tyr Asp Arg Asp Glu Trp Pro Met Ala Met Cys
65                  70                  75                  80

Ala Glu Gly Gly Thr Gly Ala Asp Ile Ala Tyr Ile Ser Pro Ser Asp
                85                  90                  95

Asn Arg Gly Ala Gly Ser Trp Val Ser Asn Gln Leu Glu Lys Tyr Glu
            100                 105                 110

Asp Gly Thr Lys Ile Leu Phe Ile Val Lys
        115                 120

<210> SEQ ID NO 2
<211> LENGTH: 118
<212> TYPE: PRT
<213> ORGANISM: Paenibacillus sp-62605

<400> SEQUENCE: 2

Asn Asp Thr Ser Val Thr Thr Ser Ser Thr Glu Ala Asp Val Lys Ile
1               5                   10                  15

Val Phe Pro Ser Asp Arg Phe Pro Glu Thr Ala Lys His Ile Lys Asp
            20                  25                  30

Ala Ile Ala Ala Gly Glu Ser Pro Ile Cys Thr Ile Asp Arg Asp Gly
        35                  40                  45

Ala Glu Glu Asn Arg Lys Glu Ser Leu Lys Gly Ile Ala Thr Lys Lys
    50                  55                  60

Gly Tyr Asp Arg Asp Glu Trp Pro Met Ala Met Cys Ala Glu Gly Gly
65                  70                  75                  80

Ala Gly Ala Asp Ile Ala Tyr Ile Thr Pro Ser Asp Asn Arg Gly Ala
                85                  90                  95

Gly Ser Trp Val Gly Asn Gln Leu Glu Lys Tyr Thr Asp Gly Thr Arg
            100                 105                 110

Val Glu Phe Val Val Glu
        115

<210> SEQ ID NO 3
<211> LENGTH: 115
<212> TYPE: PRT
<213> ORGANISM: BACILLUS SP-62738

<400> SEQUENCE: 3

Ser Glu Thr Ala Asp Ser Lys Gly Tyr Asp Gln Val Val Glu Leu Pro
1               5                   10                  15

Ala Asp Lys Tyr Pro Glu Thr Ala Ala His Ile Lys Asn Ala Ile Ala
            20                  25                  30

Lys Gly Lys Thr Asp Met Cys Thr Ile Asp Arg Lys Gly Ala Lys Asp
        35                  40                  45

Arg Arg Lys Gln Ser Leu Ala His Ile Pro Thr Lys Lys Gly Tyr Asp
    50                  55                  60

Arg Asp Glu Phe Pro Met Ala Phe Cys Lys Glu Gly Gly Ser Gly Ala
```

```
                65                  70                  75                  80
Asp Ile Glu Tyr Ile Ser Pro Glu Asp Asn Arg Gly Ala Gly Ser Tyr
                    85                  90                  95

Ile Gly Asn Lys Val Glu Asn Leu Lys Asp Gly Thr Arg Val Lys Ile
            100                 105                 110

Ala Val Asn
        115

<210> SEQ ID NO 4
<211> LENGTH: 120
<212> TYPE: PRT
<213> ORGANISM: Bacillus pumilus

<400> SEQUENCE: 4

Gln Leu Glu Gln Ser Lys Gln Glu Thr Thr Asn Ser Ser Tyr Asp Lys
1               5                   10                  15

Thr Ile His Phe Pro Ser Asp Arg Tyr Pro Glu Thr Ala Lys His Ile
            20                  25                  30

Glu Glu Ala Ile Asp Glu Gly His Ser Ser Val Cys Thr Ile Asp Arg
        35                  40                  45

Lys His Ser Asp Glu Gln Arg Asp Gln Ser Leu His Gly Ile Pro Thr
    50                  55                  60

Lys Arg Gly Tyr Asp Arg Asp Glu Trp Pro Met Ala Met Cys Lys Glu
65                  70                  75                  80

Gly Gly Thr Gly Ala Ser Val Lys Tyr Ile Ser Pro Ser Asp Asn Arg
                85                  90                  95

Gly Ala Gly Ser Trp Val Gly His Gln Leu Ser Asp Asp Pro Asp Gly
            100                 105                 110

Thr Arg Ile Gln Phe Ile Ile Asp
        115                 120

<210> SEQ ID NO 5
<211> LENGTH: 249
<212> TYPE: PRT
<213> ORGANISM: Bacillus horikoshii

<400> SEQUENCE: 5

Val Glu Asp Gly Ser Ser Thr Gln Leu Ala Asn Asn Ser Thr Asn His
1               5                   10                  15

Glu Pro Ser Ile Lys Val Arg Glu Glu Thr Glu Thr Asn Ile Glu Glu
            20                  25                  30

Asn His Glu Phe Pro Arg Thr Glu Val Pro Leu Ile Arg Val Ile Asp
        35                  40                  45

Gly Asp Thr Ile Lys Val Lys Ile Asp Gly Lys Glu Glu Asn Val Arg
    50                  55                  60

Phe Leu Leu Val Asp Thr Pro Glu Thr Ser His Pro Arg Met Asn Gly
65                  70                  75                  80

Pro Gln Pro Phe Gly Pro Glu Ala Lys Glu Phe Met Glu Glu Phe Ala
                85                  90                  95

Ala Thr Gly Lys Leu Glu Leu Glu Leu Asp Val Ser Glu Arg Asp Arg
            100                 105                 110

Tyr Gly Arg Val Leu Ala Tyr Val Tyr Val Asn Gly Val Ser Ala Gln
        115                 120                 125

Glu Glu Leu Leu Lys Arg Gly Leu Ala Arg Val Ala Tyr Ile Tyr Pro
    130                 135                 140

Pro Asn Thr Arg Tyr Val Asp His Tyr Gln Ala Leu Gln Glu Lys Ala
```

```
              145                 150                 155                 160
        Gln Ala Asp Gly Val Gly Ile Trp Ser Val Glu Asn Tyr Ala Gln Asp
                        165                 170                 175

Asp Gly Phe Tyr Pro Glu Tyr Val Glu Asp Pro Asp Leu Lys Glu Ser
                        180                 185                 190

Thr Glu Lys Gln Pro Val Thr Glu Asn Cys Pro Val Lys Gly Asn Ile
                        195                 200                 205

Ser Ser Ser Gly Glu Lys Ile Tyr His Val Lys Thr Gly Ala Phe Tyr
        210                 215                 220

Glu Arg Thr Ile Pro Glu Glu Cys Phe Asn Thr Glu Glu Ala Met
        225                 230                 235                 240

Lys Ala Gly Tyr Arg Lys Ser Lys Arg
                        245

<210> SEQ ID NO 6
<211> LENGTH: 245
<212> TYPE: PRT
<213> ORGANISM: Bacillus sp-62490

<400> SEQUENCE: 6

Ser Thr Tyr Glu Glu Thr Lys Pro Ser Ser Thr Val Glu Thr Asp Glu
        1               5                   10                  15

Ile Glu Val Asp Glu Thr Gln Lys Glu Glu Ile Ile Glu Glu Thr Ser
                        20                  25                  30

Glu Ser Phe Ile Gln Ala Thr Val Val Arg Val Val Asp Gly Asp Thr
                        35                  40                  45

Val Ile Val Lys Leu Pro Asn Asn Gln Glu Glu Arg Val Arg Leu Leu
        50                  55                  60

Leu Val Asp Thr Pro Glu Ser Val His Pro Thr Lys Pro Val Gln Pro
        65                  70                  75                  80

Phe Gly Ile Glu Ser Ser Glu Phe Ala Lys Gln Leu Met Tyr Pro Gly
                        85                  90                  95

Lys Thr Val Glu Leu Glu Leu Asp Ile Asn Glu Arg Asp Lys Tyr Gly
                        100                 105                 110

Arg Leu Leu Ala Tyr Val Trp Val Gly Glu Lys Met Leu Asn Glu Leu
                        115                 120                 125

Leu Leu Glu Lys Gly Leu Ala Arg Val Ala Tyr Ile Phe Ala Pro Asn
        130                 135                 140

Thr Arg His Val Asp Arg Phe Leu Glu Ile Gln Lys Lys Ala Gln Gln
        145                 150                 155                 160

Gln Glu Leu Gly Ile Trp Ser Ile Glu Asn Tyr Ala Thr Glu Ser Gly
                        165                 170                 175

Phe Ala Glu Glu Ala Val Leu Glu Lys Gln Glu Pro Thr Lys Leu Thr
                        180                 185                 190

Lys Ala Cys Asp Asp Pro Lys Ile Lys Gly Asn His Ser Ser Ser Gly
                        195                 200                 205

Glu Leu Ile Tyr His Ile Pro Gly Gly Gln Tyr Tyr Glu Lys Thr Asn
        210                 215                 220

Pro Glu Glu Met Phe Cys Thr Glu Asp Glu Ala Leu Glu Ala Gly Tyr
        225                 230                 235                 240

Arg Lys Ser Met Arg
                        245

<210> SEQ ID NO 7
<211> LENGTH: 223
```

```
<212> TYPE: PRT
<213> ORGANISM: Bacillus sp-13390

<400> SEQUENCE: 7

Lys Glu Ser Asn Ser Lys Glu Ala Val Glu Gln Arg Phe Ile Gln Ala
1               5                   10                  15

Ser Val Val Arg Val Val Asp Gly Asp Thr Leu Ile Val Lys Leu Asp
            20                  25                  30

His Lys Lys Glu Glu Arg Val Arg Leu Leu Leu Ile Asp Thr Pro Glu
        35                  40                  45

Ser Val His Pro Asp Lys Pro Val Gln Pro Phe Gly Ile Glu Ala Ser
    50                  55                  60

Glu Met Val Lys Glu Leu Met Lys Pro Gly Asp Leu Ile His Leu Glu
65                  70                  75                  80

Leu Asp Val Ser Glu Arg Asp Lys Tyr Gly Arg Leu Leu Ala Tyr Val
                85                  90                  95

Trp Ile Glu Asp Lys Met Val Asn Glu Leu Leu Leu Glu Lys Gly Phe
            100                 105                 110

Ala Arg Val Ala Tyr Val Tyr Ala Pro Asn Thr Lys Tyr Val Asp Gln
        115                 120                 125

Phe Tyr Asp Ile Gln Lys Gln Ala Gln Glu Arg Gly Ile Gly Ile Trp
    130                 135                 140

Ser Leu Glu Asn Tyr Val Val Asp Arg Gly Phe Asn Glu Glu Val Tyr
145                 150                 155                 160

Leu Glu Lys Asp Asn Pro Ser His Ser Asp Leu Ser Cys Ser Asn Pro
                165                 170                 175

Met Ile Lys Gly Asn His Ser Ser Arg Gly Asp Phe Ile Tyr His Val
            180                 185                 190

Pro Glu Gly Gln Tyr Tyr Asp Gln Thr Asn Ala Glu Met Phe Cys
        195                 200                 205

Thr Glu Glu Ala Lys Ala Ala Gly Tyr Arg Lys Ser Met Lys
    210                 215                 220

<210> SEQ ID NO 8
<211> LENGTH: 210
<212> TYPE: PRT
<213> ORGANISM: Jeotgalibacillus sp-13376

<400> SEQUENCE: 8

Asp Lys Pro Glu Arg Leu Asn Ala Val Val Thr Asn Val Val Asp Gly
1               5                   10                  15

Asp Thr Ile Asp Val Lys Thr Glu Asp Gly Ser Ile Glu Arg Val Arg
            20                  25                  30

Leu Leu Leu Ile Asp Thr Pro Glu Thr Lys His Pro Gln Met Gly Val
        35                  40                  45

Gln Pro Phe Gly His Glu Ala Ser Ile Tyr Thr Glu Ser Ala Leu Leu
    50                  55                  60

Gly Glu Lys Ile Gln Leu Glu Phe Asp Val Ser Glu Arg Asp Arg Tyr
65                  70                  75                  80

Gly Arg Val Leu Ala Tyr Ile Trp His Gln Asp Glu Leu Phe Asn Gln
                85                  90                  95

Thr Leu Ile Glu Lys Gly Leu Ala Arg Val Ser Ile Tyr Pro Pro Asp
            100                 105                 110

Ile Lys Tyr Val Asp Glu Phe Glu Lys Ile Gln Glu Glu Ala Arg Lys
        115                 120                 125
```

Ser Glu Leu Gly Ile Trp Ser Leu Gln Asn Tyr Val Thr Lys Lys Gly
    130                 135                 140

Tyr Glu Arg Lys Leu Asp Gln Ser Lys Asp Glu Ile Ile Gln Pro
145                 150                 155                 160

Asp Gly Cys Thr Ile Lys Gly Asn Ile Asn Ser Lys Gly Glu Lys Ile
                165                 170                 175

Tyr His Asp Thr Asn Ser Arg Ser Tyr Ser Gln Thr Ile Pro Glu Glu
                180                 185                 190

Trp Phe Cys Thr Ile Glu Glu Ala Lys Ala Ala Gly Phe Arg Ala Pro
                195                 200                 205

Arg Asn
    210

<210> SEQ ID NO 9
<211> LENGTH: 231
<212> TYPE: PRT
<213> ORGANISM: Bacillus sp-62738

<400> SEQUENCE: 9

Ser Thr Asn Lys Gln Glu Pro Ser Gln Ala Thr Thr Lys Gln Glu Ser
1               5                   10                  15

Asn Gln Thr Gln Asn Lys Thr Ser Asn Gly Gln Gln Ser Tyr Asn
                20                  25                  30

Ile Glu Asp Ile Ala Lys Asn Tyr Lys Gly Gln Lys Val Val Glu Ile
                35                  40                  45

Asn Gly Asn Lys Ala Asp Phe Thr Gln Asp Gln Leu Asp Lys Val Gln
        50                  55                  60

Leu Lys Asn Thr Asn Pro Thr Trp Gln Glu Phe Ser Asn Leu Asp Ser
65                  70                  75                  80

Lys Asn Arg Val Gly Val Ala Thr Ala Leu Ile Gly Lys Glu Ile Gln
                    85                  90                  95

Pro Lys Glu Lys Arg Asp Glu Arg Leu Asn Thr Lys Pro Thr Gly Trp
                100                 105                 110

His Gln Lys Lys Leu Ser Asp Gly Ser Thr Leu Phe Asp Arg Ser His
            115                 120                 125

Leu Ile Gly Tyr Gln Leu Thr Gly Gln Asn Asp Asn Pro Lys Asn Leu
    130                 135                 140

Met Thr Gly Thr Lys Asp Phe Asn Arg His Ser Met Leu Lys Tyr Glu
145                 150                 155                 160

Asn Met Val Asp Lys Glu Val Glu Lys Gly Ser Tyr Val Leu Tyr Glu
                165                 170                 175

Val Lys Pro Val Phe Ile Gly Asp Glu Leu Val Ala Arg Gly Val Gln
                180                 185                 190

Met Lys Ala Lys Thr Val Asn Asn His Leu Asp Phe Asn Val Phe
            195                 200                 205

Cys Phe Asn Val Gln Asp Gly Val Glu Ile Asp Tyr Lys Asp Gly Thr
        210                 215                 220

Ser Lys Leu Val Asn Lys Gln
225                 230

<210> SEQ ID NO 10
<211> LENGTH: 268
<212> TYPE: PRT
<213> ORGANISM: Streptomyces iakyrus

<400> SEQUENCE: 10

```
Arg Ser Leu Leu Asp Leu Leu Lys Pro Pro Thr Gln His Gln Glu Gln
1               5                   10                  15

Thr Ser Arg Ser Gly Ser Ile Ser Gln Ser Ala Ala Leu Asp Leu Tyr
            20                  25                  30

Ser Asn Gln Gln Lys Gln Ala Ser Phe Asp Gly Cys Ala Glu Leu Phe
        35                  40                  45

Pro Ala Ala Lys Pro Ile Asn Val Ala Thr Val Pro Ala Thr Met Asn
50                  55                  60

Pro Met Ala Leu Cys Ser Asp Asn Phe Ala Val Leu Tyr Ser Gln Thr
65                  70                  75                  80

Ser Lys Thr Pro Leu Ile Val Val Glu Arg Leu Asn Ala Ser Gln Leu
                85                  90                  95

Gln Asp Ala Lys Gly Glu Glu Arg Thr Asn Gln Phe Tyr Pro Asp Pro
            100                 105                 110

Arg Ile Pro Lys Ser Gly Arg Ala Glu Leu Ser Asp Tyr Arg Gly Gln
            115                 120                 125

His Pro Ala Val Asp Arg Gly His Gln Ser Pro Ala Ala Asp Ala Pro
        130                 135                 140

Asn Pro Asn Ala Met Ala Gln Ser Phe Ala Leu Ser Asn Met Val Pro
145                 150                 155                 160

Gln Asp Pro Thr Asn Asn Arg Lys Ile Trp Ser Lys Val Glu Ser Asp
                165                 170                 175

Val Arg Lys Phe Ala Lys Arg Ala Asp Gly Asn Val Phe Val Phe Thr
            180                 185                 190

Gly Pro Leu Phe Asp Ser Gly His Ser Thr Ile Gly Glu Asn Lys Val
            195                 200                 205

Trp Val Pro Thr Arg Leu Phe Lys Leu Val Tyr Asp Ala Ser Ser Lys
210                 215                 220

Arg Ala Trp Ala Tyr Val Leu Pro Asn Ala Glu Thr Arg Ile Glu Lys
225                 230                 235                 240

Pro Met Asp Tyr Asp Ala Phe Val Lys Ser Thr Gly Leu Lys Leu Leu
                245                 250                 255

Gly Asn Leu Pro Ile Ser Gly Ser Val Gly Arg Thr
                260                 265

<210> SEQ ID NO 11
<211> LENGTH: 245
<212> TYPE: PRT
<213> ORGANISM: Streptococcus infantis

<400> SEQUENCE: 11

Ser Asn Ala Thr Pro Gln Thr Gln Val Asn Gln Lys Ser Gln Ser Leu
1               5                   10                  15

Asp Thr Pro Ser Gln Lys Leu Ala Glu Ser Val Leu Thr Asp Ser Val
            20                  25                  30

Lys Lys Gln Ile Lys Gly Thr Leu Glu Trp Asn Gly Ser Gly Ala Phe
        35                  40                  45

Ile Val Asn Gly Asn Lys Thr Asn Leu Asp Ala Lys Val Ser Ser Lys
    50                  55                  60

Pro Tyr Ala Asp Asn Lys Thr Lys Thr Val Gly Gly Thr Val Pro
65                  70                  75                  80

Thr Val Ala Asn Ala Leu Met Ser Lys Ala Thr Arg Gln Tyr Lys Asp
                85                  90                  95

Arg Glu Glu Thr Gly Asn Gly Ser Thr Ser Trp Thr Pro Ala Gly Trp
            100                 105                 110
```

```
His Gln Val Lys Asn Leu Lys Gly Thr Tyr Asn His Ala Val Asp Arg
            115                 120                 125

Gly His Leu Leu Gly Tyr Ala Leu Ile Gly Gly Leu Asp Gly Phe Asp
        130                 135                 140

Ala Ser Thr Ser Asn Pro Lys Asn Ile Ala Val Gln Thr Ala Trp Ala
145                 150                 155                 160

Asn Gln Ala Arg Ala Glu Asp Ser Thr Gly Gln Asn Tyr Tyr Glu Ser
                165                 170                 175

Leu Val Arg Lys Ala Leu Asp Gln Asn Lys Arg Val Arg Tyr Arg Val
            180                 185                 190

Thr Leu Leu Tyr Ala Thr Glu Glu Asp Leu Val Pro Ser Ala Ser Gln
            195                 200                 205

Ile Glu Ala Lys Ser Ser Asp Gly Glu Leu Glu Phe Asn Val Val Val
            210                 215                 220

Pro Asn Val Gln Lys Gly Ile Gln Leu Asp Tyr Arg Thr Gly Lys Val
225                 230                 235                 240

Thr Val Thr Lys Asn
            245

<210> SEQ ID NO 12
<211> LENGTH: 110
<212> TYPE: PRT
<213> ORGANISM: Bacillus sp-62599

<400> SEQUENCE: 12

Ala Ser Ser Tyr Asp Ala Thr Leu Thr Phe Pro Ser Asp Lys Tyr Pro
1               5                  10                  15

Tyr Thr Ala Asp His Ile Arg Asp Ala Ile Ala Gly Gln Ser Ser
            20                  25                  30

Ile Cys Thr Ile Asp Arg Asp Gly Ala Glu Gln Asn Arg Glu Glu Ser
            35                  40                  45

Leu Arg Gly Ile Pro Thr Lys Lys Gly Tyr Asp Arg Asp Glu Trp Pro
        50                  55                  60

Met Ala Met Cys Glu Glu Gly Gly Ala Gly Ala Asp Val Arg Tyr Val
65                  70                  75                  80

Pro Ser Ser Asp Asn Arg Gly Ser Gly Ala Trp Val Gly Asn Gln Leu
                85                  90                  95

Ser Lys Tyr Pro Asp Gly Thr Arg Val Lys Phe Tyr Val Pro
            100                 105                 110

<210> SEQ ID NO 13
<211> LENGTH: 251
<212> TYPE: PRT
<213> ORGANISM: Bacillus akibai

<400> SEQUENCE: 13

Ser Thr Asp Glu Asn Lys Glu Asp Ile Leu Ile Glu Thr Ser Ser Ala
1               5                  10                  15

Val Glu Thr Asp Glu Val Glu Val Asp Glu Gln Glu His Lys Glu Glu
            20                  25                  30

Ser Pro Glu Glu Ser Asn Gly Thr Phe Ile Gln Ala Thr Val Val Arg
            35                  40                  45

Val Val Asp Gly Asp Thr Val Ile Val Lys Leu Pro Asn Asn Thr Glu
        50                  55                  60

Glu Arg Val Arg Leu Leu Leu Ile Asp Thr Pro Glu Ser Val His Pro
65                  70                  75                  80
```

Thr Lys Pro Val Gln Pro Phe Gly Leu Glu Ala Ser Glu Phe Ala Lys
                85                  90                  95

Glu Leu Met Tyr Pro Gly Lys Thr Val Glu Leu Glu Leu Asp Ile Asn
            100                 105                 110

Glu Arg Asp Arg Tyr Gly Arg Leu Leu Ala Tyr Val Trp Ile Gly Asp
        115                 120                 125

Glu Met Leu Asn Glu Leu Leu Leu Glu Asn Gly Leu Ala Arg Val Ala
    130                 135                 140

Tyr Ile Phe Ala Pro Asn Thr Arg His Val Asp Arg Phe Tyr Glu Ile
145                 150                 155                 160

Gln Lys Lys Ala Gln Gln Gln Ala Ile Gly Ile Trp Ser Ile Glu Asn
                165                 170                 175

Tyr Ala Thr Glu Gly Gly Phe Ala Glu Glu Val Asp Leu Glu Lys Gln
            180                 185                 190

Glu Pro Ser Lys Leu Ala Asn Ala Cys Asp Asp Pro Lys Ile Lys Gly
        195                 200                 205

Asn His Ser Ser Ser Gly Asp Leu Ile Tyr His Ile Pro Gly Gly Gln
    210                 215                 220

Tyr Tyr Glu Lys Thr Asn Pro Glu Glu Met Phe Cys Thr Glu Glu Glu
225                 230                 235                 240

Ala Lys Glu Ala Gly Tyr Arg Lys Ser Met Arg
                245                 250

<210> SEQ ID NO 14
<211> LENGTH: 125
<212> TYPE: PRT
<213> ORGANISM: Paenibacillus xylanexedens

<400> SEQUENCE: 14

Gly Gly Glu Trp Pro Glu Ile Pro Asn Pro Phe Gly Gly Thr Asn
1               5                   10                  15

Lys Ser Val Asp His Thr Ile Thr Phe Pro Ser Glu Arg Tyr Pro Glu
            20                  25                  30

Thr Ala Lys His Ile Lys Ala Ala Ile Lys Ala Gly His Ser Asp Val
        35                  40                  45

Cys Thr Ile Asp Arg Asn Gly Ala Glu Gly Asn Arg Asp Leu Ser Leu
    50                  55                  60

Lys Gly Val Pro Val Lys Lys Gly Lys Asp Arg Asp Glu Trp Pro Met
65                  70                  75                  80

Ala Met Cys Ala Glu Gly Gly Thr Gly Ala Asp Ile Gln Tyr Ile Thr
                85                  90                  95

Pro Lys Asp Asn Arg Gly Ala Gly Ser Trp Val Gly Asn Gln Leu Ser
            100                 105                 110

Thr Tyr Pro Asp Gly Thr Arg Val Lys Phe Val Val Lys
        115                 120                 125

<210> SEQ ID NO 15
<211> LENGTH: 182
<212> TYPE: PRT
<213> ORGANISM: Fictibacillus sp-62719

<400> SEQUENCE: 15

Leu Pro Pro Gly Thr Pro Thr Lys Ser Ala Ala Gln Ser Gln Leu Asn
1               5                   10                  15

Ala Leu Val Val Lys Thr Glu Gly Thr Met Thr Gly Tyr Ser Arg Asp
            20                  25                  30

-continued

Leu Phe Pro His Trp Ser Ser Gln Gly Gly Cys Asp Thr Arg Gln
                35                  40                  45

Val Val Leu Lys Arg Asp Ala Asp Ser Phe Ser Gly Asn Cys Pro Val
 50                  55                  60

Thr Ser Gly Ser Trp Tyr Ser Tyr Tyr Asp Gly Ile Thr Ile Thr Asn
 65                  70                  75                  80

Pro Ser Asp Leu Asp Ile Asp His Val Val Pro Leu Ala Glu Ala Trp
                85                  90                  95

Arg Ser Gly Ala Ser Ser Trp Thr Thr Asp Arg Arg Glu Ala Phe Ala
                100                 105                 110

Asn Asp Leu Thr Gly Pro Gln Leu Ile Ala Val Thr Ala Ser Ser Asn
                115                 120                 125

Arg Ser Lys Gly Asp Gln Asp Pro Ser Thr Trp Lys Pro Thr Arg Thr
130                 135                 140

Ala Ala Gly Cys Gly Tyr Ala Lys Trp Trp Ile Gln Thr Lys Tyr Asn
145                 150                 155                 160

Trp Gly Leu Asn Leu Gln Ser Ala Glu Lys Thr Ser Leu Gln Ser Met
                165                 170                 175

Leu Asn Thr Cys Thr Tyr
                180

<210> SEQ ID NO 16
<211> LENGTH: 182
<212> TYPE: PRT
<213> ORGANISM: Bacillus algicola

<400> SEQUENCE: 16

Phe Pro Pro Gly Thr Pro Ser Lys Ser Glu Ala Gln Ser Gln Leu Asn
1               5                   10                  15

Ser Leu Thr Val Gln Ser Glu Gly Ser Met Ser Gly Tyr Ser Arg Asp
                20                  25                  30

Lys Phe Pro His Trp Ile Gly Gln Gly Asn Gly Cys Asp Thr Arg Gln
                35                  40                  45

Leu Val Leu Gln Arg Asp Ala Asp Tyr Tyr Ser Gly Asp Cys Pro Val
 50                  55                  60

Thr Ser Gly Lys Trp Tyr Ser Tyr Phe Asp Gly Val Thr Val Tyr Asp
 65                  70                  75                  80

Pro Ser Asp Leu Asp Ile Asp His Met Val Pro Met Ala Glu Ala Trp
                85                  90                  95

Arg Ser Gly Ala Ser Ser Trp Ser Thr Gln Lys Arg Glu Asp Phe Ala
                100                 105                 110

Asn Asp Leu Ser Gly Pro His Leu Ile Ala Val Thr Ala Ser Ser Asn
                115                 120                 125

Arg Ser Lys Gly Asp Gln Asp Pro Ser Thr Trp Lys Pro Thr Arg Tyr
130                 135                 140

Gly Ala His Cys Gly Tyr Ala Lys Trp Trp Ile Asn Thr Lys Tyr Val
145                 150                 155                 160

Tyr Asp Leu Thr Leu Gln Ser Ser Glu Lys Thr Glu Leu Gln Ser Met
                165                 170                 175

Leu Asn Thr Cys Ser Tyr
                180

<210> SEQ ID NO 17
<211> LENGTH: 182
<212> TYPE: PRT

<213> ORGANISM: Exiguobacterium sp. NG55

<400> SEQUENCE: 17

```
Phe Pro Pro Asn Ile Pro Ser Lys Ala Asp Ala Leu Thr Lys Leu Asn
1               5                   10                  15

Ala Leu Thr Val Lys Asn Glu Gly Ser Met Thr Gly Tyr Ser Arg Asp
            20                  25                  30

Ile Phe Pro His Trp Ser Ser Gln Gly Ser Gly Cys Asn Thr Arg His
        35                  40                  45

Ile Val Leu Lys Arg Asp Ala Asp Ser Val Val Asp Gln Cys Pro Val
    50                  55                  60

Thr Thr Gly Ser Trp Tyr Ser Tyr Tyr Asp Gly Leu Thr Phe Thr Ser
65                  70                  75                  80

Ala Ser Asp Ile Asp Ile Asp His Val Val Pro Leu Ala Glu Ala Trp
            85                  90                  95

Arg Ser Gly Ala Ser Ser Trp Thr Thr Thr Lys Arg Gln Ser Phe Ala
            100                 105                 110

Asn Asp Leu Asn Gly Pro Gln Leu Ile Ala Val Ser Ala Ser Ser Asn
            115                 120                 125

Arg Ser Lys Gly Asp Gln Asp Pro Ser Thr Trp Gln Pro Pro Arg Thr
130                 135                 140

Gly Ala Arg Cys Ala Tyr Ala Lys Met Trp Val Glu Thr Lys Ser Arg
145                 150                 155                 160

Trp Gly Leu Ser Leu Gln Ser Ala Glu Lys Ser Ala Leu Thr Thr Ala
                165                 170                 175

Ile Asn Ala Cys Ser Tyr
            180
```

<210> SEQ ID NO 18
<211> LENGTH: 182
<212> TYPE: PRT
<213> ORGANISM: Metagenome from environmental sample J

<400> SEQUENCE: 18

```
Leu Pro Pro Asn Ile Pro Ser Lys Ala Asp Ala Leu Thr Lys Leu Asn
1               5                   10                  15

Ala Leu Thr Val Gln Thr Glu Gly Pro Met Thr Gly Tyr Ser Arg Asp
            20                  25                  30

Leu Phe Pro His Trp Ser Ser Gln Gly Asn Gly Cys Asn Thr Arg His
        35                  40                  45

Val Val Leu Lys Arg Asp Ala Asp Ser Val Val Asp Thr Cys Pro Val
    50                  55                  60

Thr Thr Gly Arg Trp Tyr Ser Tyr Tyr Asp Gly Leu Val Phe Thr Ser
65                  70                  75                  80

Ala Ser Asp Ile Asp Ile Asp His Val Val Pro Leu Ala Glu Ala Trp
            85                  90                  95

Arg Ser Gly Ala Ser Ser Trp Thr Ser Thr Lys Arg Gln Ser Phe Ala
            100                 105                 110

Asn Asp Leu Asn Gly Pro Gln Leu Ile Ala Val Ser Ala Thr Ser Asn
            115                 120                 125

Arg Ser Lys Gly Asp Gln Asp Pro Ser Thr Trp Gln Pro Pro Arg Ala
130                 135                 140

Gly Ala Arg Cys Ala Tyr Ala Lys Met Trp Val Glu Thr Lys Ser Arg
145                 150                 155                 160

Trp Gly Leu Thr Leu Gln Ser Ser Glu Lys Ala Ala Leu Gln Thr Ala
                165                 170                 175
```

```
                         165                 170                 175

Ile Asn Ala Cys Ser Tyr
            180

<210> SEQ ID NO 19
<211> LENGTH: 216
<212> TYPE: PRT
<213> ORGANISM: Streptomyces thermoalcalitolerans

<400> SEQUENCE: 19

Cys Thr Glu Asp Thr Gly Gly Pro Gly Thr Pro Glu Lys Thr Ala Ala
1               5                   10                  15

Gly Ala Ala Leu Ala Ala Val Glu Glu Leu Pro Val Lys Gly Arg Ala
            20                  25                  30

Pro Lys Thr Gly Tyr Glu Arg Glu Lys Phe Gly Arg Ala Trp Ala Asp
        35                  40                  45

Thr Asp Ser Asn Gly Cys Arg Thr Arg Asp Asp Ile Leu Lys Arg Asp
    50                  55                  60

Leu Glu Gln Val Arg Phe Thr Asp Gly Thr Cys Lys Val Ser Tyr Gly
65                  70                  75                  80

Val Leu Ala Ser Asp Pro Tyr Ser Gly Lys Glu Ile Val Phe Arg Arg
                85                  90                  95

Gly His Ser Gln Ile Asp Ile Asp His Val Val Ala Leu Ser Asp Ala
            100                 105                 110

Trp Gln Lys Gly Ala Lys Tyr Trp Asp Ala Ser Lys Arg Ile Ala Leu
        115                 120                 125

Ala Asn Asp Pro Leu Asn Leu Ala Val Asp Ala Arg Thr Asn Arg
    130                 135                 140

Ala Lys Gly Asp Gly Asp Thr Ala Thr Trp Leu Pro Pro Asn Lys Ala
145                 150                 155                 160

Tyr Arg Cys Gln Tyr Val Ala Arg Gln Val Ala Val Lys Lys Lys Tyr
                165                 170                 175

Glu Leu Trp Val Thr Ala Ala Glu Lys Ala Ala Met Lys Arg Val Leu
            180                 185                 190

Ser Thr Cys Pro Asp Gln Lys Leu Pro Ser Gly Gly Thr Pro Thr Lys
        195                 200                 205

Ala Pro Glu Arg Phe Arg Ala Gln
    210                 215

<210> SEQ ID NO 20
<211> LENGTH: 200
<212> TYPE: PRT
<213> ORGANISM: Metagenome from environmental sample C

<400> SEQUENCE: 20

Ser Leu Pro Asp Tyr Ala Ser Pro Ile Ser Thr Pro Thr Ser Gly Leu
1               5                   10                  15

Ala Thr Pro Ala Ser Asp Ala Ser Pro Ser Arg Lys Asp Arg Thr
            20                  25                  30

Asp Tyr Asp Tyr Glu Leu Val Phe Pro Ser Asp Lys Tyr Pro Glu Thr
        35                  40                  45

Ala Leu His Ile His Gly Ala Ile Glu Met Gly Tyr Ser Asp Val Cys
    50                  55                  60

Thr Ile Asp Arg Gly Gly Ala Glu Gln Asn Arg Lys Glu Ser Leu Ala
65                  70                  75                  80

Gly Ile Glu Thr Arg Gln Gly Tyr Asp Arg Asp Glu Trp Pro Met Ala
```

-continued

```
                85                  90                  95
Met Cys Gly Glu Gly Gly Ala Gly Ala Ser Val Ala Tyr Ile Asp Ala
            100                 105                 110

Gly Asp Asn Arg Gly Ala Gly Ser Trp Val Gly Asn Gln Leu Lys Glu
            115                 120                 125

Tyr Pro Asp Gly Thr Arg Ile Leu Phe Ile Val Asp Lys Pro Ala Asn
    130                 135                 140

Leu Phe Pro Ala Gln Ser Pro Asn Ala Ser Ser Gln Pro Ala Asp Asp
145                 150                 155                 160

Ala Glu Val Tyr Tyr Lys Asn Cys Thr Ala Val Arg Glu Ala Gly Lys
                165                 170                 175

Ala Pro Leu His Lys Gly Glu Pro Gly Tyr Ala Ala His Leu Asp Arg
            180                 185                 190

Asp Gly Asn Gly Val Ala Cys Glu
        195                 200

<210> SEQ ID NO 21
<211> LENGTH: 27
<212> TYPE: PRT
<213> ORGANISM: Artificial
<220> FEATURE:
<223> OTHER INFORMATION: Bacillus clausii secretion signal

<400> SEQUENCE: 21

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25
```

POLYPEPTIDES

CROSS-REFERENCE TO RELATED APPLICATIONS

This application is a 35 U.S.C. 371 national application of international application no. PCT/EP2016/074115 filed Oct. 7, 2016, which claims priority or the benefit under 35 U.S.C. 119 of Danish application nos. PA 2015 00615, PA 2015 00617 and PA 2015 00618, each filed Oct. 7, 2015. The content of each application is fully incorporated herein by reference.

REFERENCE TO A SEQUENCE LISTING

This application contains a Sequence Listing in computer readable form, which is incorporated herein by reference.

FIELD OF THE INVENTION

The present invention relates to new polypeptides having deoxyribonuclease (DNase) activity, nucleotides encoding the polypeptide, as well as methods of producing the polypeptides. The present invention also relates to detergent composition comprising a DNase, a laundering method and the use of DNase.

BACKGROUND OF INVENTION

Microorganisms generally live attached to surfaces in many natural, industrial, and medical environments, encapsulated by extracellular substances including biopolymers and macromolecules. The resulting layer of slime encapsulated microorganism is termed a biofilm. Biofilms are the predominant mode of growth of bacteria in the natural environment, and bacteria growing in biofilms exhibit distinct physiological properties. Compared to their planktonically grown counterparts, the bacteria in a biofilm are more resistant to antibiotics, UV irradiation, detergents and the host immune response.

A biofilm may include one or more microorganisms, including gram-positive and gram-negative bacteria, algae, protozoa, and/or yeast or filamentous fungi and viruses and/or bacteriophage. Examples of problematic biofilms are dental plaque, infections on medical implants, but also the initial fouling on ship hulls. Biofilms are attributed to the pathogenesis of many infections in humans and are a significant problem in industry in terms of biofouling of exposed surfaces, where biofilm colonisation can form the base component of a localised ecosystem which can disrupt and interfere with industrial processes and components.

When laundry items like T-shirts or sportswear are used, they are exposed to bacteria from the body of the user and from the rest of the environment in which they are used. Some of these bacteria are capable of adhering to the laundry item and form a biofilm on the item. The presence of bacteria implies that the laundry items become sticky and therefore soil adheres to the sticky areas. This soil has shown difficult to remove by commercially available detergent compositions. Further, when very dirty laundry items are washed together with less dirty laundry items the dirt present in the wash liquor tend to stick to the biofilm. As a result hereof the laundry item is more "soiled" after wash than before wash. Further, these bacteria are a source of bad odor, which develops after use of the laundry item. The bad odor (malodor) is difficult to remove and may remain even after wash. The reason for this bad odor is adhesion of bacteria to the textile surface. Because of the adhesion to the textile, the bacteria may remain even after wash, and continue to be a source of bad odor.

International patent applications WO2011/098579 (University of Newcastle) and WO2014/087011 (Novozymes NS) relate to deoxyribonuclease compounds and methods for biofilm disruption and prevention.

SUMMARY OF THE INVENTION

The invention relates to polypeptides having DNase (deoxyribonuclease) activity. One aspect of the invention relates to a polypeptide having DNase activity, selected from the group consisting of:

(a) a polypeptide having at least 60% sequence identity to SEQ ID NO: 1, 2, 3, 4, 5, 6, 7, 8, 9, 10, 11, 12, 13, 14, 15, 16, 17, 18, 19 or 20, (b) a variant of the mature polypeptide of SEQ ID NO: 1, 2, 3, 4, 5, 6, 7, 8, 9, 10, 11, 12, 13, 14, 15, 16, 17, 18, 19 or 20 comprising a substitution, deletion, and/or insertion at one or more positions; and (c) a fragment of the polypeptide of (a) or (b), that has DNase activity.

In another aspect the invention relates to detergent compositions comprising a polypeptide having DNase activity and preferably a detergent adjunct ingredient. One aspect of the invention relates to a detergent composition comprising a polypeptide having at least 60% sequence identity to the polypeptide of SEQ ID NO: 1, 2, 3, 4, 5, 6, 7, 8, 9, 10, 11, 12, 13, 14, 15, 16, 17, 18, 19 or 20 and a detergent adjunct.

The invention further relates to a cleaning or laundering method for cleaning or laundering an item comprising the steps of:

a. Exposing an item to a wash liquor comprising a polypeptide having DNase activity selected from the group consisting of the polypeptide of SEQ ID NO: 1, 2, 3, 4, 5, 6, 7, 8, 9, 10, 11, 12, 13, 14, 15, 16, 17, 18, 19 and 20 or a polypeptide having at least 60% sequence identity hereto or a detergent composition comprising the polypeptides;

b. Completing at least one wash cycle; and c. Optionally rinsing the item, wherein the item is a textile.

In addition is claimed the use of DNase for preventing, reducing or removing the biofilm of an item.

The present invention further relates to methods of producing the polypeptides.

Sequences

SEQ ID NO 1 mature polypeptide obtained from *Paenibacillus* sp-62212

SEQ ID NO 2 mature polypeptide obtained from *Paenibacillus* sp-62605

SEQ ID NO 3 mature polypeptide obtained from *Bacillus* sp-62738

SEQ ID NO 4 mature polypeptide obtained from *Bacillus pumilus*

SEQ ID NO 5 mature polypeptide obtained from *Bacillus horikoshii*

SEQ ID NO 6 mature polypeptide obtained from *Bacillus* sp-62490

SEQ ID NO 7 mature polypeptide obtained from *Bacillus* sp-13390

SEQ ID NO 8 mature polypeptide obtained from *Jeotgalibacillus* sp-13376

SEQ ID NO 9 mature polypeptide obtained from *Bacillus* sp-62738

SEQ ID NO 10 mature polypeptide obtained from *Streptomyces iakyrus*
SEQ ID NO 11 mature polypeptide obtained from *Streptococcus infantis*
SEQ ID NO 12 mature polypeptide obtained from *Bacillus* sp-62599
SEQ ID NO 13 mature polypeptide obtained from *Bacillus akibai*
SEQ ID NO 14 mature polypeptide obtained from *Paenibacillus xylanexedens*
SEQ ID NO 15 mature polypeptide obtained from *Fictibacillus* sp-62719
SEQ ID NO 16 mature polypeptide obtained from *Bacillus algicola*
SEQ ID NO 17 mature polypeptide obtained from *Exiguobacterium* sp. NG55
SEQ ID NO 18 mature polypeptide obtained from Metagenome from environmental sample J
SEQ ID NO 19 mature polypeptide obtained from *Streptomyces thermoalcalitolerans*
SEQ ID NO 20 mature polypeptide obtained from Metagenome from environmental sample C
SEQ ID NO 21 is *Bacillus clausii* secretion signal Definitions Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Biofilm: A biofilm is any group of microorganisms in which cells stick to each other on a surface, such as a textile, dishware or hard surface. These adherent cells are frequently embedded within a self-produced matrix of extracellular polymeric substance (EPS). Biofilm EPS is a polymeric conglomeration generally composed of extracellular DNA, proteins, and polysaccharides.

Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from free-floating bacteria of the same species, as the dense and protected environment of the film allows them to cooperate and interact in various ways. One benefit of this environment is increased resistance to detergents and antibiotics, as the dense extracellular matrix and the outer layer of cells protect the interior of the community. On laundry biofilm producing bacteria can be found among the following species: *Acinetobacter* sp., *Aeromicrobium* sp., *Brevundimonas* sp., *Microbacterium* sp., *Micrococcus luteus, Pseudomonas* sp., *Staphylococcus epidermidis*, and *Stenotrophomonas* sp.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, synthetic DNA, or a combination thereof.

Color difference (L value): A Lab color space is a color-opponent space with dimension L for lightness. L value, $L^*$ represents the darkest black at $L^*=0$, and the brightest white at $L^*=100$. In the context of the present invention L value is also referred to as color difference.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Deep cleaning: By the term "deep cleaning" is meant disruption or removal of a biofilm or components of a biofilm such as polysaccharides, proteins, DNA, soil or other components present in the biofilm.

Detergent adjunct ingredient: The detergent adjunct ingredient is different to the DNase of this invention. The precise nature of these additional adjunct components, and levels of incorporation thereof, will depend on the physical form of the composition and the nature of the operation for which it is to be used. Suitable adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

Detergent Composition: The term "detergent composition" refers to compositions that find use in the removal of undesired compounds from items to be cleaned, such as textiles. The detergent composition may be used to e.g. clean textiles for both household cleaning and industrial cleaning. The terms encompass any materials/compounds selected for the particular type of detergent composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pre-treatment). In addition, to containing a DNase of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

DNase (deoxyribonuclease): The term "DNase" means a polypeptide with DNase activity that catalyzes the hydrolytic cleavage of phosphodiester linkages in the DNA backbone, thus degrading DNA. The term "DNases" and the expression "a polypeptide with DNase activity" are used interchangeably throughout the application. For purposes of the present invention, DNase activity is determined according to the procedure described in the Assay I. In one aspect, the polypeptides of the present invention have at least 20%, e.g., at least 40%, at least 50%, at least 60%, at least 70%, at least 80%, at least 90%, at least 95%, or at least 100% of the DNase activity of the polypeptides with SEQ ID NO: 1, 2, 3, 4, 5, 6, 7, 8, 9, 10, 11, 12, 13, 14, 15, 16, 17, 18, 19 or 20.

Enzyme Detergency benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide or domain; wherein the fragment has DNase activity.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved wash performance: The term "improved wash performance" is defined herein as an enzyme displaying an increased wash performance in a detergent composition relative to the wash performance of same detergent composition without the enzyme e.g. by increased stain removal or less redeposition. The term "improved wash performance" includes wash performance in laundry.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

Malodor: By the term "malodor" is meant an odor which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal. Another example of malodor can be the odor from spices, which sticks to items for example curry or other exotic spices which smells strongly. One way of measuring the ability of an item to adhere malodor is by using Assay II disclosed herein.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide., The mature polypeptide of the DNases of the invention is shown in SEQ ID NO: 1, 2, 3, 4, 5, 6, 7, 8, 9, 10, 11, 12, 13, 14, 15, 16, 17, 18, 19 and 20.

Mature polypeptide coding sequence: The term "mature polypeptide coding sequence" means a polynucleotide that encodes a mature polypeptide having DNase activity.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Pharmaceutical adjunct ingredient means any pharmaceutical excipient suitable for formulating the pharmaceutical compound. Such excipients, carriers, vehicles etc. are well known to those of skill in the art and are described in text books such as Remington's Pharmaceutical Sciences, Mack Publishing Co., Easton, Pa., 1985. Pharmaceutically acceptable excipients which are suitable for use in tablet formulations include, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. Tablets may be uncoated or they may be coated by known techniques to delay disintegration and absorption in the gastrointestinal tract and thereby provide a sustained action over a longer period.

For example, a time delay material such as glyceryl monostearate or glyceryl distearate may be employed. For hard gelatin capsule formulations, the active ingredient can be mixed with an inert solid diluent, for example, calcium carbonate, calcium phosphate or kaolin. For soft gelatin capsule formulations the active ingredient can be mixed with water or an oil medium, for example peanut oil, liquid paraffin or olive oil. Excipients suitable for the manufacture of aqueous suspensions include suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters obtained from fatty acids and a hexitol such as polyoxyethylene sorbitol monooleate, or condensation products of ethylene oxide with partial esters obtained from fatty acids and hexitol anhydrides, for example polyethylene sorbitan monooleate. Aqueous suspensions may also contain one or more preservatives, for example benzoates, such as ethyl, or n-propyl p-hydroxybenzoate, one or more colouring agents, one or more flavouring agents, and one or more sweetening agents, such as sucrose or saccharin. Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavouring agents may be added. These compositions may be preserved by the addition of an antioxidant such as ascorbic acid.

Remission value: Wash performance may be expressed as a Remission value of the stained swatches. After washing and rinsing the swatches are spread out flat and allowed to air dry at room temperature overnight. All washes swatches are evaluated the day after the wash. Light reflectance evaluations of the swatches may be done using a Macbeth Color Eye 7000 reflectance spectrophotometer with very small aperture. The measurements are made without UV in the incident light and remission at 460 nm is extracted.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows: (Identical Residues×100)/(Length of Alignment–Total Number of Gaps in Alignment). For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EM-BOSS: The European Molecular Biology Open Software Suite, Rice et al., 2000, supra), prefer-ably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows: (Identical Deoxyribonucleotides×100)/(Length of Alignment–Total Number of Gaps in Alignment).

Stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having DNase activity.

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g. polyamide fiber, acrylic fiber, polyester fiber, polyvinyl chloride fiber, polyurethane fiber, polyurea fiber, aramid fiber), and/or cellulose-containing fiber (e.g. rayon/viscose, ramie, flax/linen, jute, cellulose acetate fiber, lyocell). Fabric may be conventional washable laundry, for example stained household laundry. When the term fabric or garment is used it is intended to include the broader term textiles as well. In the context of the present invention, the term "textile" also covers fabrics.

Variant: The term "variant" means a polypeptide having same activity as the parent enzyme comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. In the context of the present invention, a variant of an identified DNase has the enzymatic activity of the parent, i.e. the capacity of catalyzing the hydrolytic cleavage of phosphodiester linkages in the DNA backbone (deoxyribonuclease activity). In one embodiment, the deoxyribonuclease activity of the variant is increased with reference to the parent DNase, e.g. the polypeptide of SEQ ID NO: 1, 2, 3, 4, 5, 6, 7, 8, 9, 10, 11, 12, 13, 14, 15, 16, 17, 18, 19 and 20.

Wash cycle: The term "wash cycle" is defined herein as a washing operation wherein textiles are immersed in the wash liquor, mechanical action of some kind is applied to the textile in order to release stains and to facilitate flow of wash liquor in and out of the textile and finally the superfluous wash liquor is removed. After one or more wash cycles, the textile is generally rinsed and dried.

Wash liquor: The term "wash liquor" is defined herein as the solution or mixture of water and detergent components optionally including the enzyme of the invention.

Wash time: The term "wash time" is defined herein as the time it takes for the entire washing process; i.e. the time for the wash cycle(s) and rinse cycle(s) together.

Whiteness: The term "Whiteness" is defined herein as a broad term with different meanings in different regions and for different consumers. Loss of whiteness can e.g. be due to greying, yellowing, or removal of optical brighteners/hueing agents. Greying and yellowing can be due to soil redeposition, body soils, colouring from e.g. iron and copper ions or dye transfer. Whiteness might include one or several issues from the list below: colourant or dye effects; incomplete stain removal (e.g. body soils, sebum etc.); redeposition (greying, yellowing or other discolorations of the object) (removed soils reassociate with other parts of textile, soiled or unsoiled); chemical changes in textile during application; and clarification or brightening of colours.

DETAILED DESCRIPTION OF THE INVENTION

The polypeptides of the present invention having deoxyribonuclease (DNase) activity can be used for preventing or removing biofilm on items such as textiles and/or fabric. A polypeptide having DNase activity or a deoxyribonuclease (DNase) is any enzyme that catalyzes the hydrolytic cleavage of phosphodiester linkages in the DNA backbone, thus degrading DNA. The two terms polypeptide having DNase activity and DNase are used interchangeably. The present invention relates to DNases obtainable from *Paenibacillus* sp-62212, *Paenibacillus* sp-62605, *Bacillus* sp-62738, *Bacillus pumilus, Bacillus horikoshii, Bacillus* sp-62490, *Bacillus* sp-13390, *Jeotgalibacillus* sp-13376, *Bacillus* sp-62738, *Streptomyces iakyrus, Streptococcus infantis, Bacillus* sp-62599, *Bacillus akibai, Paenibacillus xylanexedens, Fictibacillus* sp-62719, *Bacillus algicola, Exiguobacterium* sp. NG55, Metagenome from environmental sample J, *Streptomyces thermoalcalitolerans*, Metagenome from environmental sample C. The DNase of the present invention includes the polypeptides of SEQ ID NOS: 1, 2, 3, 4, 5, 6, 7, 8, 9, 10, 11, 12, 13, 14, 15, 16, 17, 18, 19 and 20 and polypeptides having sequence identity to the polypeptides of any of the polypeptide selected from the group consisting of SEQ ID NO: 1, 2, 3, 4, 5, 6, 7, 8, 9, 10, 11, 12, 13, 14, 15, 16, 17, 18, 19 or 20 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptides have DNase activity.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 1.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 2.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 3.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 4.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 5.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 6.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 7.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 8.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 9.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 10.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 11.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 12.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 13.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 14.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 15.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 16.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 17.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 18.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 19.

One embodiment relates to a polypeptide having DNase activity wherein the polypeptide has at least at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO 20.

In a preferred aspect of the invention, the DNase is obtained from *Paenibacillus* sp-62212 and comprises the polypeptide sequence with SEQ ID NO 1. In a preferred aspect of the invention the DNase is obtained from *Paeni-* bacillus sp-62605 and comprises the polypeptide sequence with SEQ ID NO 2. In a preferred aspect of the invention the DNase is obtained from *Bacillus* sp-62738 and comprises the polypeptide sequence with SEQ ID NO 3. In a preferred aspect of the invention the DNase is obtained from *Bacillus pumilus* and comprises the polypeptide sequence with SEQ ID NO 4. In a preferred aspect of the invention the DNase is obtained from *Bacillus horikoshii* and comprises the polypeptide sequence with SEQ ID NO 5. In a preferred aspect of the invention the DNase is obtained from *Bacillus* sp-62490 and comprises the polypeptide sequence with SEQ ID NO 6. In a preferred aspect of the invention the DNase is obtained from *Bacillus* sp-13390 and comprises the polypeptide sequence with SEQ ID NO 7. In a preferred aspect of the invention the DNase is obtained from *Jeotgalibacillus* sp-13376 and comprises the polypeptide sequence with SEQ ID NO 8. In a preferred aspect of the invention the DNase is obtained from *Bacillus* sp-62738 and comprises the polypeptide sequence with SEQ ID NO 9. In a preferred aspect of the invention the DNase is obtained from *Streptomyces iakyrus* and comprises the polypeptide sequence with SEQ ID NO 10. In a preferred aspect of the invention the DNase is obtained from *Streptococcus infantis* and comprises the polypeptide sequence with SEQ ID NO 11. In a preferred aspect of the invention the DNase is obtained from *Bacillus* sp-62599 and comprises the polypeptide sequence with SEQ ID NO 12. In a preferred aspect of the invention the DNase is obtained from *Bacillus akibai* and comprises the polypeptide sequence with SEQ ID NO 13. In a preferred aspect of the invention the DNase is obtained from *Paenibacillus xylanexedens* and comprises the polypeptide sequence with SEQ ID NO 14. In a preferred aspect of the invention the DNase is obtained from *Fictibacillus* sp-62719 and comprises the polypeptide sequence with SEQ ID NO 15. In a preferred aspect of the invention the DNase is obtained from *Bacillus algicola* and comprises the polypeptide sequence with SEQ ID NO 16. In a preferred aspect of the invention the DNase is obtained from *Exiguobacterium* sp. NG55 and comprises the polypeptide sequence with SEQ ID NO 17. In a preferred aspect of the invention the DNase is obtained from Metagenome from environmental sample J and comprises the polypeptide sequence with SEQ ID NO 18. In a preferred aspect of the invention the DNase is obtained from *Streptomyces thermoalcalitolerans* and comprises the polypeptide sequence with SEQ ID NO 19. In a preferred aspect of the invention the DNase is obtained from Metagenome from environmental sample C and comprises the polypeptide sequence with SEQ ID NO 20.

Biofilm can develop on textile when microorganisms are present on an item and stick together on the item. Some microorganisms tend to adhere to the surface of items such as textiles. Some microorganisms adhere to such surfaces and form a biofilm on the surface. The biofilm may be sticky and the adhered microorganisms and/or the biofilm may be difficult to remove. Furthermore the biofilm adhere soil due to the sticky nature of the biofilm. The commercial laundry detergent compositions available on the marked do not remove such adhered microorganisms or biofilm.

The present invention relates to polypeptides having DNase activity and the use of such polypeptides for preventing, reducing or removing a biofilm from an item, such as textiles. In one embodiment of the invention the polypeptides having DNase activity are used for preventing, reducing or removing the stickiness of an item. In one embodiment of the invention, the polypeptides having DNase activity improves whiteness of an item, such as a textile. In one embodiment the polypeptides of the invention having DNase activity helps maintaining the colour on textiles. When textiles are repeatedly washed the colours tend to be less bright. In one embodiment the polypeptides of the invention having DNase activity have an improved effect of maintaining the colour of coloured textiles even after repeated washes. In one embodiment the polypeptides of the invention reduce the colouring of non-coloured part of the same or additional textile present in the wash.

The polypeptide having DNase activity can further be used for pretreating stains on textile such as textile with a pronounced amount of biofilm adhered to the textile.

The invention also relates to the use of polypeptides having DNase activity for preventing, reducing or removing redeposition of soil during a wash cycle. When the polypeptides are used for example in the laundering of textile, the polypeptides may hinder deposition of soil present in the wash liquor to deposit on the textile.

Further, the invention relates to the use of a polypeptide having DNase activity for preventing, reducing or removing the adherence of soil to an item. In one embodiment, the item is textile. When the soil does not adhere to the item, the item appears cleaner. Thus, the invention further relates to the use of polypeptides having DNase activity for maintaining or improving the whiteness of the item.

When items like T-shirts or sportswear are used, they are exposed to bacteria from the body of the user and from the rest of the environment in which they are used. This may cause malodor on the item even after the item is washed. The present invention therefore also relates removal or reduction of malodor on textile. The malodor may be caused by bacteria producing compounds with an unpleasant smell. One example of such unpleasant smelling compounds is E-2-nonenal. The malodor can be present on newly washed textile which is still wet. Or the malodor can be present on newly washed textile, which has subsequently been dried. The malodor may also be present on textile, which has been stored for some time after wash. The present invention concerns the reduction or removal of malodor such as E-2-nonenal from wet or dry textile.

The polypeptides of the invention having DNase activity i.e. the DNases of the invention have very good cleaning performance in detergent. Examples of beneficial effects of the DNases with SEQ ID NOS: 1, 2, 3, 4, 5, 6, 7, 8, 9, 10, 11, 12, 13, 14, 15, 16, 17, 18, 19 and 20 are the deep-cleaning effect as shown in example 2, preventing laundry in becoming grey and/or remove malodor. The polypeptides comprising SEQ ID NO 1, 2, 3, 4, 5, 6, 7, 8, 9, 10, 11, 12, 13, 14, 15, 16, 17, 18, 19 and 20 have DNase activity and have deep cleaning effect in detergents.

Yet another embodiment relates to the use of a DNase, selected from the group consisting of SEQ ID NOS 1, 2, 3, 4, 5, 6, 7, 8, 9, 10, 11, 12, 13, 14, 15, 16, 17, 18, 19 and 20, or a polypeptide having at least 80% sequence identity hereto for reducing malodor from laundry and/or textile, for anti-redeposition and for maintaining or improving the whiteness of a textile Yet another embodiment relates to the use of a DNase, selected from the group consisting of SEQ ID NO 1 or a polypeptide having at least 80% sequence identity hereto for reducing malodor from laundry and/or textile, for anti-redeposition and for maintaining or improving the whiteness of a textile Yet another embodiment relates to the use of a DNase, selected from the group consisting of SEQ ID NO 2 or a polypeptide having at least 80% sequence identity hereto for reducing malodor from laundry and/or textile, for anti-redeposition and for maintaining or improving the whiteness of a textile Yet another embodiment relates to the use of a DNase, selected from the group consisting of SEQ ID NO 3 or a polypeptide having at least 80% sequence identity hereto for reducing malodor from laundry and/or textile, for anti-redeposition and for maintaining or improving the whiteness of a textile Yet another embodiment relates to the use of a DNase, selected from the group consisting of SEQ ID NO 4 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 5 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 6 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 7 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 8 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 9 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 10 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 11 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 12 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 13 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 14 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 15 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 16 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 17 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 18 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 19 or a polypeptide having at least 80% sequence identity hereto for reducing malodor from laundry and/or textile, for anti-redeposition and for maintaining or improving the whiteness of a textile.

Yet another embodiment relates to the use of a DNase, selected from the group consisting of SEQ ID NO 20 or a polypeptide having at least 80% sequence identity hereto for reducing malodor from laundry and/or textile, for anti-redeposition and for maintaining or improving the whiteness of a textile.

The invention relates to polypeptides having a sequence identity to any of the polypeptides of SEQ ID NO: 1, 2, 3, 4, 5, 6, 7, 8, 9, 10, 11, 12, 13, 14, 15, 16, 17, 18, 19 or 20 of at least 60% which have DNase activity and wherein the polypeptides are used for preventing, reducing or removing a biofilm from an item.

The invention relates to polypeptides having a sequence identity to the polypeptide shown in SEQ ID NO: 1 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 2 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 3 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 4 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 5 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 6 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 7 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 8 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 9 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 10 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 11 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 12 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 13 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 14 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 15 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 16 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 17 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 18 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 19 of at least 60%, such as at least 70%, such as at least 80%, such as at least 90% such as at least 95% or 100%, which have DNase activity and wherein the polypeptide is capable of preventing, reducing or removing a biofilm from an item.

The invention relates to polypeptides having a sequence identity to the polypeptide shown in SEQ ID NO: 20 of at least 60%, such as at least 70%, such as at least 80%, such as at least 90% such as at least 95% or 100%, which have DNase activity and wherein the polypeptide is capable of preventing, reducing or removing a biofilm from an item.

The deep cleaning effect of the polypeptides having DNases activity with SEQ ID NO 1, 2, 3, 4, 5, 6, 7, 8, 9, 10, 11, 12, 13, 14, 15, 16, 17, 18, 19 and 20 is shown in Example 2.

As described By the term "deep cleaning" is meant disruption or removal of a biofilm or components of a biofilm such as polysaccharides, proteins, DNA, soil or other components present in the biofilm.

A polypeptide of the present invention preferably comprises or consists of the amino acid sequence of any of SEQ ID NO: 1, 2, 3, 4, 5, 6, 7, 8, 9, 10, 11, 12, 13, 14, 15, 16, 17, 18, 19 and 20 or an allelic variant thereof; or is a fragment thereof having DNase activity. In another aspect, the polypeptide comprises or consists of the polypeptide with SEQ ID NO: 1, 2, 3, 4, 5, 6, 7, 8, 9, 10, 11, 12, 13, 14, 15, 16, 17, 18, 19 or 20.

In another aspect, the polypeptide comprises or consists of the polypeptide with SEQ ID NO: 1. In another aspect, the polypeptide comprises or consists of the polypeptide with SEQ ID NO: 2. In another aspect, the polypeptide comprises or consists of the polypeptide with SEQ ID NO: 3. In another aspect, the polypeptide comprises or consists of the polypeptide with SEQ ID NO: 4. In another aspect, the polypeptide comprises or consists of the polypeptide with SEQ ID NO: 5. In another aspect, the polypeptide comprises or consists of the polypeptide with SEQ ID NO: 6. In another aspect, the polypeptide comprises or consists of the polypeptide with SEQ ID NO: 7. In another aspect, the polypeptide comprises or consists of the polypeptide with SEQ ID NO: 8. In another aspect, the polypeptide comprises or consists of the polypeptide with SEQ ID NO: 9. In another aspect, the polypeptide comprises or consists of the polypeptide with SEQ ID NO: 10. In another aspect, the polypeptide comprises or consists of the polypeptide with SEQ ID NO: 11. In another aspect, the polypeptide comprises or consists of the polypeptide with SEQ ID NO: 12. In another aspect, the polypeptide comprises or consists of the polypeptide with SEQ ID NO: 13. In another aspect, the polypeptide comprises or consists of the polypeptide with SEQ ID NO: 14. In another aspect, the polypeptide comprises or consists of the polypeptide with SEQ ID NO: 15. In another aspect, the polypeptide comprises or consists of the polypeptide with SEQ ID NO: 16. In another aspect, the polypeptide comprises or consists of the polypeptide with SEQ ID NO: 17. In another aspect, the polypeptide comprises or consists of the polypeptide with SEQ ID NO: 18. In another aspect, the polypeptide comprises or consists of the polypeptide with SEQ ID NO: 19. In another aspect, the polypeptide comprises or consists of the polypeptide with SEQ ID NO: 20.

In an embodiment, the polypeptide has been isolated.

In another embodiment, the present invention relates to an isolated polypeptide having DNase activity encoded by a polynucleotide that hybridizes under low stringency conditions with (i) the mature polypeptide coding sequence or (ii) the full-length complement of (i) (Sambrook et al., 1989, Molecular Cloning, A Laboratory Manual, 2d edition, Cold Spring Harbor, N.Y.). In an embodiment, the polypeptide has been isolated.

In another embodiment, the present invention relates to an isolated polypeptide having DNase activity encoded by a polynucleotide that hybridizes under low-medium stringency conditions with (i) the mature polypeptide coding sequence or (ii) the full-length complement of (i). In an embodiment, the polypeptide has been isolated.

In another embodiment, the present invention relates to an isolated polypeptide having DNase activity encoded by a polynucleotide that hybridizes under medium stringency conditions with (i) the mature polypeptide coding sequence or (ii) the full-length complement of (i). In an embodiment, the polypeptide has been isolated.

In another embodiment, the present invention relates to an isolated polypeptide having DNase activity encoded by a polynucleotide that hybridizes under medium-high stringency conditions with (i) the mature polypeptide coding sequence or (ii) the full-length complement of (i). In an embodiment, the polypeptide has been isolated.

In another embodiment, the present invention relates to an isolated polypeptide having DNase activity encoded by a polynucleotide that hybridizes under high stringency conditions with (i) the mature polypeptide coding sequence or (ii) the full-length complement of (i). In an embodiment, the polypeptide has been isolated.

In another embodiment, the present invention relates to an isolated polypeptide having DNase activity encoded by a polynucleotide that hybridizes under very high stringency conditions with (i) the mature polypeptide coding sequence or (ii) the full-length complement of (i). In an embodiment, the polypeptide has been isolated.

The polynucleotides or a subsequence thereof, as well as the polypeptides of SEQ ID NO: 1, 2, 3, 4, 5, 6, 7, 8, 9, 10, 11, 12, 13, 14, 15, 16, 17, 18, 19 and 20 or a fragment thereof, may be used to design nucleic acid probes to identify and clone DNA encoding polypeptides having DNase activity from strains of different genera or species according to methods well known in the art. In particular, such probes can be used for hybridization with the genomic DNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides or at least 600 nucleotides. Both DNA and RNA probes can be used. The probes are typically labelled for detecting the corresponding gene (for example, with $^{32}P$, $^{3}H$, $^{35}S$, biotin, or avidin). Such probes are encompassed by the present invention.

A genomic DNA library prepared from such other strains may be screened for DNA that hybridizes with the probes described above and encodes a polypeptide having DNase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with the polynucleotides encoding the polypeptides of the invention or a subsequence thereof, the carrier material is used in a Southern blot.

For purposes of the present invention, hybridization indicates that the polynucleotide hybridizes to a labelled nucleic acid probe corresponding to (i) the mature polypeptide coding sequence; (ii) the full-length complement thereof; or (iii) a subsequence thereof; under very low, low stringency conditions, low-medium stringency conditions, medium stringency conditions, medium-high stringency conditions, high stringency conditions to very high stringency conditions. Molecules to which the nucleic acid probe hybridizes under these conditions can be detected using, for example, X-ray film or any other detection means known in the art.

In another embodiment, the present invention relates to variants of the polypeptides of SEQ ID NO: 1, 2, 3, 4, 5, 6, 7, 8, 9, 10, 11, 12, 13, 14, 15, 16, 17, 18, 19 or 20 comprising a substitution, deletion, and/or insertion at one or more (e.g., several) positions. In an embodiment, the number of amino acid substitutions, deletions and/or insertions introduced into the polypeptides of SEQ ID NO: 1, 2, 3, 4, 5, 6, 7, 8, 9, 10, 11, 12, 13, 14, 15, 16, 17, 18, 19 or 20 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 1 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 2 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 3 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 4 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 5 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 6 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 7 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 8 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 9 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 10 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 11 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 12 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 13 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 14 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 15 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 16 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 17 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 18 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 19 is up to 10, e.g., 1, 2, 3, 4, 5, 6, 7, 8, 9, or 10.

In an embodiment, the number of amino acid substitutions, deletions and/or insertions introduced into the polypeptides of SEQ ID NO: 20 is up to 10, e.g., 1, 2, 3, 4, 5, 6, 7, 8, 9, or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for DNase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17:

893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Polynucleotides

The present invention also relates to polynucleotides encoding a polypeptide, as described herein. In an embodiment, the polynucleotide encoding the polypeptide of the present invention has been isolated. The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* ylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression. The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Paenibacillus* sp-62212, *Paenibacillus* sp-62605, *Bacillus* sp-62738, *Bacillus pumilus, Bacillus horikoshii, Bacillus* sp-62490, *Bacillus* sp-13390, *Jeotgalibacillus* sp-13376, *Bacillus* sp-62738, *Streptomyces iakyrus, Streptococcus infantis, Bacillus* sp-62599, *Bacillus akibai, Paenibacillus xylanexedens, Penicillium reticulisporum, Fictibacillus* sp-62719, *Bacillus algicola, Exiguobacterium* sp. NG55, Metagenome from environmental sample J, *Streptomyces thermoalcalitolerans* or Metagenome from environmental sample C cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

In one embodiment, the invention further comprises producing the polypeptide by cultivating the recombinant host cell further comprising a polynucleotide encoding a second polypeptide of interest; preferably an enzyme of interest; more preferably a secreted enzyme of interest; even more preferably a hydrolase, isomerase, ligase, lyase, oxidoreductase, or a transferase; and most preferably the secreted enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.

In one embodiment, the second polypeptide of interest is heterologous or homologous to the host cell.

In one embodiment, the recombinant host cell is a fungal host cell; preferably a filamentous fungal host cell; more preferably an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell; most preferably an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

In one embodiment, the recombinant host cell is a bacterial host cell; preferably a prokaryotic host cell; more preferably a Gram-positive host cell; even more preferably a *Bacillus, Clostridium, Enterococcus, Geobacillus, Lactobacillus, Lactococcus, Oceanobacillus, Staphylococcus, Streptococcus*, or *Streptomyces* host cell; and most preferably a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* host cell.

In one embodiment, a method of producing the second polypeptide of interest comprises cultivating the host cell under conditions conducive for production of the second polypeptide of interest.

In one embodiment, the method further comprises recovering the second polypeptide of interest.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells are grown to saturation, incubated under carbon-limiting conditions to allow protein synthesis. In some embodiments, the cell-killed whole broth or composition contains the spent cell culture medium, extracellular enzymes, and killed microbial cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Compositions

The present invention further concerns a detergent composition comprising polypeptides having DNase activity of the invention and preferably a detergent adjunct ingredient. The detergent composition can be used for preventing, reducing or removing biofilm from an item, for preventing, reducing or removing the stickiness of an item, for pretreating stains on the item, for preventing, reducing or removing redeposition of soil during a wash cycle, for reducing or removing adherence of soil to an item, for maintaining or improving the whiteness of an item and for preventing, reducing or removing malodor from an item, such as E-2-nonenal as described in Assay II). The detergent compositions comprising the polypeptides of the present invention overcomes the problems of the prior art as described above.

The polypeptides of the invention having DNase activity are useful in powder and liquid detergents. In one embodiment of the invention, the detergent composition comprises a DNase, selected from the group consisting of SEQ ID NOS 1, 2, 3, 4, 5, 6, 7, 8, 9, 10, 11, 12, 13, 14, 15, 16, 17, 18, 19 and 20 and a detergent adjunct.

In one embodiment of the invention, the detergent composition comprises a polypeptide having DNase activity wherein the polypeptide comprises the polypeptide shown in SEQ ID NO 1 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 2 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 3 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 4 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 5 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 6 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 7 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 8 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 9 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 10 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 11 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 12 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 13 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 14 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 15 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 16 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 17 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 18 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 19 or a polypeptide having at least 70%, such as at least 80%, such as at least 90%, such as at least 95% or 100% sequence identity hereto and a detergent adjunct.

In one embodiment of the invention, the detergent composition comprises a polypeptide having DNase activity wherein the polypeptide comprises the polypeptide shown in SEQ ID NO 20 or a polypeptide having at least 70%, such as at least 80%, such as at least 90%, such as at least 95% or 100% sequence identity hereto and a detergent adjunct.

In one embodiment of the invention, the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments.

The detergent adjunct ingredient may be a surfactant. One advantage of including a surfactant in a detergent composition comprising a polypeptide having DNase activity is that the wash performance is improved. In one embodiment, the detergent adjunct ingredient is a builder or a clay soil removal/anti-redeposition agent.

In one embodiment, detergent adjunct ingredient is an enzyme. The detergent composition may comprise one or more enzymes, as specified below. The one or more enzymes may be selected from the group consisting of proteases, lipases, cutinases, amylases, carbohydrases, cellulases, pectinases, mannanases, arabinases, galactanases, xylanases and oxidases. Specific enzymes suitable for the detergent compositions of the invention are described below.

In one embodiment, the detergent composition is capable of reducing adhesion of bacteria selected from the group consisting of *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp. to a surface, or releasing the bacteria from a surface to which they adhere.

Biofilm growth in laundry items may originate from many organisms as described previously. One particular abundant bacterium in biofilm originates from *Brevundimonas*. As shown in the examples the DNases of the invention are particularly effective in reducing the growth of the bacterium and reducing the malodor, stickiness and re-deposition coursed by these bacteria. One embodiment of the invention relates to the use of a DNase, selected from the group consisting of SEQ ID NOS 1, 2, 3, 4, 5, 6, 7, 8, 9, 10, 11, 12, 13, 14, 15, 16, 17, 18, 19 and 20 in reduction of malodor and reducing stickiness and re-deposition. One embodiment relates to the use in laundering of a DNase, selected from the group consisting of SEQ ID NOS 1, 2, 3, 4, 5, 6, 7, 8, 9, 10, 11, 12, 13, 14, 15, 16, 17, 18, 19 and 20 wherein the DNase reducing adhesion of bacteria from *Brevundimonas*.

In one embodiment of the invention, the surface is a textile surface. The textile can be made of cotton, Cotton/Polyester, Polyester, Polyamide, Polyacryl and/or silk.

The detergent composition may be formulated as a bar, a homogenous tablet, and a tablet having two or more layers, a pouch having one or more compartments, a regular or compact powder, a granule, a paste, a gel, or a regular, compact or concentrated liquid. The detergent composition can be a liquid detergent, a powder detergent or a granule detergent.

The DNases of the invention are suitable for use in cleaning such as laundry. The invention further relates a method for laundering an item, which method comprises the steps of:

a. Exposing an item to a wash liquor comprising a polypeptide selected from the group consisting of polypeptides comprising SEQ ID NOS 1, 2, 3, 4, 5, 6, 7, 8, 9, 10, 11, 12, 13, 14, 15, 16, 17, 18, 19 and 20 having DNase activity or a detergent composition comprising the polypeptide;

b. Completing at least one wash cycle; and c. Optionally rinsing the item, wherein the item is a textile.

The pH of the liquid solution is in the range of 1 to 11, such as in the range 5.5 to 11, such as in the range of 7 to 9, in the range of 7 to 8 or in the range of 7 to 8.5.

The wash liquor may have a temperature in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C. In one embodiment the temperature of the wash liquor is 30° C.

In one embodiment of the invention, the method for laundering an item further comprises draining of the wash liquor or part of the wash liquor after completion of a wash cycle. The wash liquor can then be re-used in a subsequent wash cycle or in a subsequent rinse cycle. The item may be exposed to the wash liquor during a first and optionally a second or a third wash cycle. In one embodiment the item is rinsed after being exposed to the wash liquor. The item can be rinsed with water or with water comprising a conditioner. The invention further concerns an item washed according to the inventive method. The detergent composition comprising a polypeptide selected from the group consisting of polypeptides comprising SEQ ID NOS 1, 2, 3, 4, 5, 6, 7, 8, 9, 10, 11, 12, 13, 14, 15, 16, 17, 18, 19 and 20 having DNase activity can be used for releasing or removing a biofilm or preventing biofilm formation.

The DNases of the invention may be added to a wash liquor.

Thus, one embodiment of the invention relates to a detergent composition comprising one or more anionic surfactants; an enzyme selected from the group consisting of: a protease, a lipase, a cutinase, an amylase, a carbohydrase, a cellulase, a pectinase, a mannanase, an arabinase, a galactanase, a xylanase, and an oxidase; and a DNase, selected from the group consisting of SEQ ID NOS 1, 2, 3, 4, 5, 6, 7, 8, 9, 10, 11, 12, 13, 14, 15, 16, 17, 18, 19 and 20.

One embodiment further relates to a washing method for textile comprising:

a. Exposing a textile to a wash liquor comprising a DNase or a detergent composition comprising at least one of the DNases, b. completing at least one wash cycle; and c. optionally rinsing the textile, wherein the DNases are selected from the group consisting of SEQ ID NOS 1, 2, 3, 4, 5, 6, 7, 8, 9, 10, 11, 12, 13, 14, 15, 16, 17, 18, 19 and 20.

Another embodiment relates to a textile washed according to the inventive method.

The concentration of the DNase in the wash liquor is typically in the range of 0.00004-100 ppm enzyme protein, such as in the range of 0.00008-100, in the range of 0.0001-100, in the range of 0.0002-100, in the range of 0.0004-100, in the range of 0.0008-100, in the range of 0.001-100 ppm enzyme protein, 0.01-100 ppm enzyme protein, preferably 0.05-50 ppm enzyme protein, more preferably 0.1-50 ppm enzyme protein, more preferably 0.1-30 ppm enzyme protein, more preferably 0.5-20 ppm enzyme protein, and most preferably 0.5-10 ppm enzyme protein.

The DNase of the present invention may be added to a detergent composition in an amount corresponding to at least 0.002 mg of DNase protein, such as at least 0.004 mg of DNase protein, at least 0.006 mg of DNase protein, at least 0.008 mg of DNase protein, at least 0.01 mg of DNase protein, at least 0.1 mg of protein, preferably at least 1 mg of protein, more preferably at least 10 mg of protein, even more preferably at least 15 mg of protein, most preferably at least 20 mg of protein, and even most preferably at least 25 mg of protein. Thus, the detergent composition may comprise at least 0.00008% DNase protein, preferably at least 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% of DNase protein.

Enzymes including present in a detergent of the invention may be stabilized using conventional stabilizing agents, e.g. a polyols such as propylene glycol or glycerol, a sugar or sugar alcohol and different salts such as NaCl and KCl. Proteases present in the detergent of the invention may be stabilized using lactic acid, formic acid, boric acid, or a boric acid derivative, e.g., an aromatic borate ester, or a phenyl boronic acid derivative such as 4-formylphenyl boronic acid, or a peptide aldehyde such as di-, tri- or tetrapeptide aldehydes or aldehyde analogues (either of the form B1-B0-R wherein, R is H, CH3, CX3, CHX2, or CH2X (X=halogen), B0 is a single amino acid residue (preferably with an optionally substituted aliphatic or aromatic side chain); and B1 consists of one or more amino acid residues (preferably one, two or three), optionally comprising an N-terminal protection group, or as described in WO09118375, WO98/13459) or a protease inhibitor of the protein type such as RASI, BASI, WASI (bifunctional alpha-amylase/subtilisin inhibitors of rice, barley and wheat) or CI2 or SSI. The composition may be formulated as described in e.g. WO 92/19709, WO 92/19708 and U.S. Pat. No. 6,472,364. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), Nickel (II), and oxovanadium (IV)).

In one embodiment, the polypeptides are stabilized using peptide aldehydes or ketones Suitable peptide aldehydes are described in WO94/04651, WO95/25791, WO98/13458, WO98/13459, WO98/13460, WO98/13461, WO98/13462, WO07/141736, WO07/145963, WO09/118375, WO10/055052 and WO11/036153. A polypeptide of the present invention may also be incorporated in the detergent formulations disclosed in WO 97/07202, which is hereby incorporated by reference.

In another embodiment, the polypeptides are stabilized using a phenyl boronic acid derivative is 4-formylphenyl-boronic acid (4-FPBA) with the following formula:

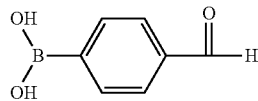 [SMILES: O=Cc1ccc(B(O)O)cc1]

The detergent compositions may comprise two or more stabilizing agents e.g. such as those selected from the group consisting of propylene glycol, glycerol, 4-formylphenyl boronic acid and borate.

The detergent compositions may comprise two or more stabilizing agents e.g. such as those selected from the group consisting of propylene glycol, glycerol, 4-formylphenyl boronic acid and borate.

The stabilizing agent(s) is preferably present in the detergent composition in a quantity of from 0.001 to about 5.0 wt %, from 0.01 to about 2.0 wt %, from 0.1 to about 3 wt % or from 0.5% to about 1.5 wt %.

Liquid Detergent Composition

The DNases of the invention may also be formulated in liquid laundry compositions such as a liquid laundry compositions composition comprising:

a) at least 0.005 mg of active DNase protein per litre detergent wherein the DNase is selected from a polypeptide comprising any of SEQ ID NOS 2, 4, 6, 8, 10, 12, 14, 16, 18, 20, 22, 24, 26, 28, 30, 32, 34, 36, 38, 40, 42 or a DNase having at least 80% sequence identity hereto, b) 2 wt % to 60 wt % of at least one surfactant, and c) 5 wt % to 50 wt % of at least one builder The surfactant may be selected among nonionic, anionic and/or amphoteric surfactants as described above, preferably anionic or nonionic surfactants but also amphoteric surfactants may be used. In general, bleach-stable surfactants are preferred. Preferred anionic surfactants are sulphate surfactants and in particular alkyl ether sulphates, especially C-9-15 alcohol ethersulfates, C12-15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

The anionic surfactants are preferably added to the detergent in the form of salts. Suitable cations in these salts are alkali metal ions, such as sodium, potassium and lithium and ammonium salts, for example (2-hydroxyethyl)ammonium, bis(2-hydroxyethyl)ammonium and tris(2-hydroxyethyl) ammonium salts. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. Commercially available nonionic surfactants includes Plurafac™, Lutensol™ and Pluronic™ range from BASF, Dehypon™ series from Cognis and Genapol™ series from Clariant.

The builder is preferably selected among phosphates, sodium citrate builders, sodium carbonate, sodium silicate, sodium aluminosilicate (zeolite). Suitable builders are alkali metal or ammonium phosphates, polyphosphates, phosphonates, polyphosphonates, carbonates, bicarbonates, borates, citrates, and polycarboxylates. Citrate builders, e.g., citric acid and soluble salts thereof (particularly sodium salt), are polycarboxylate builders. Citrates can be used in combination with zeolite, silicates like the BRITESIL types, and/or layered silicate builders. The builder is preferably added in an amount of about 0-65% by weight, such as about 5% to about 50% by weight. In a laundry detergent, the level of builder is typically about 40-65% by weight, particularly about 50-65% by weight, particularly from 20% to 50% by weight. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), and (carboxymethyl) inulin (CMI), and combinations thereof. Further non-limiting examples of builders include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycine-N,N-diacetic acid (MGDA), glutamic acid-N,N-diacetic acid (GLDA), 1-hydroxyethane-1,1-diphosphonic acid, N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(sulfomethyl)aspartic acid (SMAS), N-(2-sulfoethyl)-aspartic acid (SEAS), N-(sulfomethylglutamic acid (SMGL), N-(2-sulfoethyl)-glutamic acid (SEGL), N-methyliminodiacetic acid (MIDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and N'-(2-hydroxyethypethylenediamine-N,N,N'-triacetic acid (HEDTA), diethanolglycine (DEG), and combinations and salts thereof.

Phosphonates suitable for use herein include 1-hydroxyethane-1,1-diphosphonic acid (HEDP), ethylenediaminetetrakis(methylenephosphonic acid) (EDTMPA), diethylenetriaminepentakis(methylenephosphonic acid) (DTMPA or DTPMPA or DTPMP), nitrilotris(methylenephosphonic acid) (ATMP or NTMP), 2-phosphonobutane-1,2,4-tricarboxylic acid (PBTC), hexamethylenediaminetetrakis(methylenephosphonic acid) (HDTMP)

The detergent composition may also contain 0-50% by weight, such as about 5% to about 30%, of a detergent co-builder.

The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA) or polyaspartic acid.

Further exemplary builders and/or co-builders are described in, e.g., WO 09/102854, U.S. Pat. No. 5,977,053 In one preferred embodiment, the builder is a non-phosphorus based builder such as citric acid and/or methylglycine-N,N-diacetic acid (MGDA) and/or glutamic-N,N-diacetic acid (GLDA) and/or salts thereof.

The laundry composition may also be phosphate free in the instance the preferred builders includes citrate and/or methylglycine-N,N-diacetic acid (MGDA) and/or glutamic-N,N-diacetic acid (GLDA) and/or salts thereof.

One embodiment of the invention concerns a liquid laundry compositions composition comprising:

a) at least 0.005 mg of active DNase per litre of composition wherein the DNase is selected from a polypeptide comprising any of SEQ ID NOS 2, 4, 6, 8, 10, 12, 14, 16, 18, 20, 22, 24, 26, 28, 30, 32, 34, 36, 38, 40, 42 or DNases having at least 80% sequence identity hereto, b) 1% to 15% by weight of at least one surfactant wherein the surfactant is LAS, AEOS and/or SLES, and c) 5% to 50% by weight of at least one builder selected from HEDP, DTMPA or DTPMPA.

The liquid detergent composition may typically containing at least 20% by weight and up to 95% water, such as up to 70% water, up to 50% water, up to 40% water, up to 30% water, or up to 20% water. Other types of liquids, including without limitation, alkanols, amines, diols, ethers and polyols may be included in an aqueous liquid detergent. An aqueous liquid detergent may contain from 0-30% organic solvent. A liquid detergent may even be non-aqueous, wherein the water content is below 10%, preferably below 5%.

Powder Compositions

The detergent composition may also be formulated into a granular detergent for laundry or dish wash. One embodiment of the invention concerns a granular detergent composition comprising a) at least 0.005 mg of active DNase per gram of composition wherein the DNase is selected from a polypeptide comprising any of SEQ ID NOS 1, 2, 3, 4, 5, 6, 7, 8, 9, 10, 11, 12, 13, 14, 15, 16, 17, 18, 19 and 20, or a DNase having at least 80% sequence identity hereto, b) 5 wt % to 50 wt % anionic surfactant c) 1 wt % to 8 wt % nonionic surfactant, and d) 5 wt % to 40 wt % builder such as carbonates, zeolites, phosphate builder, calcium sequestering builders or complexing agents The surfactant may be selected among nonionic, anionic and/or amphoteric surfactants as described above, preferably anionic or nonionic surfactants but also amphoteric surfactants may be used. In general, bleach-stable surfactants are preferred. Preferred anionic surfactants are sulphate surfactants and in particular alkyl ether sulphates, especially C-9-15 alcohol ethersulfates, C12-15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

The anionic surfactants are preferably added to the detergent in the form of salts. Suitable cations in these salts are alkali metal ions, such as sodium, potassium and lithium and ammonium salts, for example (2-hydroxyethyl)ammonium, bis(2-hydroxyethyl)ammonium and tris(2-hydroxyethyl) ammonium salts.

Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

Commercially available nonionic surfactants includes Plurafac™, Lutensol™ and Pluronic™ range from BASF, Dehypon™ series from Cognis and Genapol™ series from Clariant.

The builder is may be non-phosphate such as citrate preferably as a sodium salt and/or zeolites. Phosphonate builder may be any of those described above.

The builder is preferably selected among phosphates and sodium citrate builders, sodium carbonate, sodium silicate, sodium aluminosilicate (zeolite) as described above. Suitable builders are described above and include alkali metal or ammonium phosphates, polyphosphates, phosphonates, polyphosphonates, carbonates, bicarbonates, borates, polyhydroxysulfonates, polyacetates, carboxylates, citrates, and polycarboxylates. Citrate builders, e.g., citric acid and soluble salts thereof (particularly sodium salt), are polycarboxylate builders. The builder is preferably added in an amount of about 0-65% by weight, such as about 5% to about 50% by weight, such as 5 to 40% by weight, such as 10 to 40% by weight, such as 10 to 30% by weight, such as 15 to 20% by weight or such as 20 to 40% by weight. The builder may be a phosphonate builder including 1-hydroxyethane-1,1-diphosphonic acid (HEDP), ethylenediaminetetra (methylenephosphonic acid) (EDTMPA), diethylenetriaminepentakis (methylenephosphonic acid) (DTMPA or DTPMPA), diethylenetriamine penta (methylenephosphonic acid) (DTPMP), aminotris(methylenephosphonic acid) (ATMP), 2-phosphonobutane-1,2,4-tricarboxylic acid (PBTC) and hexamethylenediaminetetra (methylenephosphonic acid) (HDTMP).

Preferred phosphonates includes 1-hydroxyethane-1,1-diphosphonic acid (HEDP) and/or diethylenetriaminepentakis (methylenephosphonic acid) (DTMPA or DTPMPA). The phosphonate is preferably added in an amount of about in a level of from about 0.01% to about 10% by weight, preferably from 0.1% to about 5% by weight, more preferably from 0.5% to 3% by weight of the composition.

The laundry composition may also be phosphate free in the instance the preferred builders includes citrate, carbonates and/or sodium aluminosilicate (zeolite).

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore acetyl triethyl citrate and triacetin have good hydrolytical stability in the product upon storage and are efficient bleach activators. Finally ATC is multifunctional, as the citrate released in the perhydrolysis reaction may function as a builder.

Bleach catalysts and boosters: The bleaching system may also include a bleach catalyst or booster. Some non-limiting examples of bleach catalysts that may be used in the compositions of the present invention include manganese oxalate, manganese acetate, manganese-collagen, cobalt-amine catalysts and manganese triazacyclononane (Mn-TACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds, such as iron or cobalt complexes.

In some embodiments, where a source of a peracid is included, an organic bleach catalyst or bleach booster may be used having one of the following formulae:

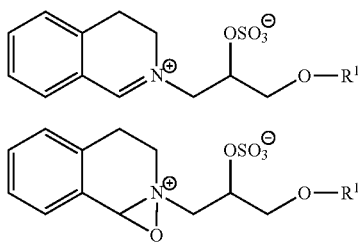

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

According to one embodiment and any of the previous embodiments the invention also relates to a detergent composition comprising;
a) at least 0.005 mg of active DNase per gram of composition wherein the DNase is selected from a polypeptide comprising any of SEQ ID NOS: 1, 2, 3, 4, 5, 6, 7, 8, 9, 10, 11, 12, 13, 14, 15, 16, 17, 18, 19, 20 or a DNase having at least 80% sequence identity hereto,
b) 10-50 wt % builder and
c) at least one bleach component, wherein the bleach is a peroxide and the bleach catalyst is a manganese compound.

The oxygen bleach is preferably percarbonate and the manganese catalyst preferably 1,4,7-trimethyl-1,4,7-triazacyclononane or manganese (III) acetate tetrahydrate According to one embodiment and any of the previous embodiments the invention also relates to a detergent composition comprising;
a) at least 0.005 mg of active DNase per gram of composition wherein the DNase is selected from a polypeptide comprising any of SEQ ID NOS: 1, 2, 3, 4, 5, 6, 7, 8, 9, 10, 11, 12, 13, 14, 15, 16, 17, 18, 19, 20 or a DNases having at least 80% sequence identity hereto,
b) 10-50 wt % builder selected from citric acid, methyl glycine-N,N-diacetic acid (MGDA) and/or glutamic-N,N-diacetic acid (GLDA) and mixtures thereof, and
c) at least one bleach component, wherein the bleach is an oxygen bleach and the bleach catalyst is a manganese compound.

The oxygen bleach is preferably percarbonate and the manganese catalyst preferably 1,4,7-trimethyl-1,4,7-triaza-cyclo-nonane or manganese (II) acetate tetrahydrate According to one embodiment and any of the previous embodiments the invention also relates to a detergent composition comprising;
a) at least 0.005 mg of active DNase per gram of composition wherein the DNase is selected from a polypeptide comprising any of SEQ ID NOS: 1, 2, 3, 4, 5, 6, 7, 8, 9, 10, 11, 12, 13, 14, 15, 16, 17, 18, 19, 20 or a DNase having at least 80% sequence identity hereto,
b) 10-50 wt % builder selected from citric acid, methyl glycine-N,N-diacetic acid (MGDA) and/or glutamic-N,N-diacetic acid (GLDA) and mixtures thereof, and
c) 0.1-40 wt %, preferably from 0.5-30 wt %, of bleaching components, wherein the bleach components are a peroxide, preferably percabonate and a metal-containing bleach catalyst preferably 1,4,7-trimethyl-1,4,7-triazacyclononane or manganese (II) acetate tetrahydrate (MnTACN).

The choice of detergent components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Hydrotropes

The detergent composition may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly (vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The detergent compositions of the invention may comprise one or more additional enzymes such as a protease, lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes NS) Carezyme Premium™ (Novozymes NS), Celluclean™ (Novozymes NS), Celluclean Classic™ (Novozymes NS), Cellusoft™ (Novozymes NS), Whitezyme™ (Novozymes NS), Clazinase™, and Puradax HA™ (Genencor International Inc.), and KAC-500(B)™ (Kao Corporation).

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those obtained from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin lentus, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases obtained from *Cellulomonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those obtained from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V41, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes NS), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes NS), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases

Suitable amylases which can be used together with the DNases of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase obtained from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase obtained from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+ G475K;
S125A+N128C+K178L+T182G+Y305R+G475K; or
S125A+N128C+T131I+T165I+K178L+T182G+Y305R+ G475K, wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar/Effectenz™, Powerase and Preferenz S100 (from Genencor International Inc./ DuPont).

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment obtained therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase according to the invention also includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago*, *Alternaria*, *Curvularia*, e.g., *C. verruculosa* and *C. inaequalis*, *Drechslera*, *Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In a preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

An oxidase according to the invention include, in particular, any laccase enzyme comprised by the enzyme classification EC 1.10.3.2, or any fragment obtained therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be obtained from plants, bacteria or fungi (including filamentous fungi and yeasts).

Suitable examples from fungi include a laccase derivable from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*, *Coprinopsis*, e.g., *C. cinerea*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, *Schytalidium*, e.g., *S. thermophilum*, *Polyporus*, e.g., *P. pinsitus*, *Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase obtained from *Coprinopsis* or *Myceliophthora* is preferred; in particular a laccase obtained from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Other Materials

Any detergent components known in the art for use in the detergent composition of the invention may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in detergents may be utilized. The choice of such ingredients is well within the skill of the artisan.

Dispersants

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3] triazol-2-yl)-2-[(E)-2-phenylvinyl]benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Tinopal CBS-X is a 4,4'-bis-(sulfostyryl)-biphenyl disodium salt also known as Disodium Distyrylbiphenyl Disulfonate. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Anti-Parasitic/Viral Compounds

The detergent composition may further comprise an antiparasitic compound can be one or more of a benzazole, such as albendazole, mebendazole and tiabendazole; an azole, such as metronidazole and tinidazole; a macrocycle, such as amphotericin B, rifampin and ivermectin; pyrantel pamoate; diethylcarbamazine; niclosamide; praziquantel; melarsopro; and eflornithine.

The antiviral compound can be one or more of a nucleoside analog reverse transcriptase inhibitor, such as acyclovir, didanosine, stavudine, zidovudine, lamivudine, abacavir, emtricitabine and entecavir; an uncoating inhibitor such as amantadine, rimantadine and pleconaril; a protease inhibitor such as saquinavir, ritonavir, indinavir, nelfinavir and amprenavir; zanamivir; oseltamivir; and rifampin. The antibacterial compound can be one or more of an aminoglycoside such as gentamicin, kanamycin and streptomycin; a beta-lactam such as penicillin, ampicillin and imipenem; a cephalosporin such as ceftazidime, a quinolone such as ciprofloxacin; a macrolide such as azithromycin, clarithromycin, dirithromycin, erythromycin, roxithromycin and telithromycin; an oxazolidinone such as linezolid; an ansamycin such as rifamycin; a sulphonamide; a tetracycline such as doxycycline; a glycopeptide such as vancomycin; sulfisoxazole, trimethoprim, novobiocin, daptomycin and linezolid.

The antifungal compound can be one or more of an azole, such as miconazole, ketoconazole, clotrimazole, econazole, omoconazole, bifonazole, butoconazole, fenticonazole, isoconazole, sertaconazole, sulconazole, tioconazole, fluconazole, itraconazole, isavuconazole, ravuconazole, posaconazole, voriconazole, terconazole and abafungin; a macrocycle, such as natamycin, rimocidin, filipin, nystatin, amphotericin B, candicin, hamycin; an allyl amine such as terbinafine, naftifine and butenafine; an echinocandin such as andidulafungin, caspofungin and micafungin; or others such as polygodial, ciclopirox, tolnaftate, benzoic acid, undecylenic acid, flucytosine and griseofulvin.

Formulation of DNases in Microcapsule

The DNases of the invention may be formulated in microcapsules or in liquid detergents comprising microcapsules. A liquid detergent composition of the invention may comprise a surfactant and a detergent builder in a total concentration of at least 3% by weight, and an enzyme, which may be a DNase, containing microcapsule, wherein the membrane of the microcapsule is produced by cross-linking of a polybranched polyamine having a molecular weight of more than 1 kDa. Encapsulating of enzymes such as DNases in a microcapsule with a semipermeable membrane having a water activity inside these capsules (prior to addition to the liquid detergent) higher than in the liquid detergent, the capsules will undergo a (partly) collapse when added to the detergent (water is oozing out), thus leaving a more concentrated and more viscous enzyme containing interior in the capsules. The collapse of the membrane may also result in a reduced permeability. This can be further utilized by addition of stabilizers/polymers, especially ones that are not permeable through the membrane. The collapse and resulting increase in viscosity will reduce/hinder the diffusion of hostile components (e.g., surfactants or sequestrants) into the capsules, and thus increase the storage stability of enzymes such as DNases in the liquid detergent. Components in the liquid detergent that are sensitive to the enzyme (e.g., components that act as substrate for the enzyme) are also protected against degradation by the enzyme. During wash the liquid detergent is diluted by water, thus increasing the water activity. Water will now diffuse into the capsules (osmosis). The capsules will swell and the membrane will either become permeable to the enzyme so they can leave the capsules, or simply burst and in this way releasing the enzyme. The concept is very efficient in stabilizing the enzymes such as the DNases of the invention against hostile components in liquid detergent, and vice versa also protects enzyme sensitive components in the liquid detergent from enzymes.

Examples of detergent components which are sensitive to, and can be degraded by, enzymes include (relevant enzyme in parenthesis): xanthan gum (xanthanase), polymers with ester bonds (lipase), hydrogenated castor oil (lipase), perfume (lipase), methyl ester sulfonate surfactants (lipase), cellulose and cellulose derivatives (e.g. CMC) (cellulase), and dextrin and cyclodextrin (amylase).

Also, sensitive detergent ingredients can be encapsulated, and thus stabilized, in the microcapsules of the invention. Sensitive detergent ingredients are prone to degradation during storage. Such detergent ingredients include bleaching compounds, bleach activators, perfumes, polymers, builder, surfactants, etc.

Generally, the microcapsules can be used to separate incompatible components/compounds in detergents.

Addition of the microcapsules to detergents can be used to influence the visual appearance of the detergent product, such as an opacifying effect (small microcapsules) or an effect of distinctly visible particles (large microcapsules). The microcapsules may also be colored.

The microcapsules can be used to reduce the enzyme dust levels during handling and processing of enzyme products.

Unless otherwise indicated, all percentages are indicated as percent by weight (% w/w) throughout the application.

Microcapsule: The microcapsules are typically produced by forming water droplets into a continuum that is non-miscible with water—i.e., typically by preparing a water-in-oil emulsion—and subsequently formation of the membrane by interfacial polymerization via addition of a cross-linking agent. After eventual curing the capsules can be harvested and further rinsed and formulated by methods known in the art. The capsule formulation is subsequently added to the detergent.

The payload, the major membrane constituents and eventual additional component that are to be encapsulated are found in the water phase. In the continuum is found components that stabilize the water droplets towards coalescence (emulsifiers, emulsion stabilizers, surfactants etc.) and the cross linking agent is also added via the continuum.

The emulsion can be prepared be any methods known in the art, e.g., by mechanical agitation, dripping processes, membrane emulsification, microfluidics, sonication etc. In some cases simple mixing of the phases automatically will result in an emulsion, often referred to as self-emulsification. Using methods resulting in a narrow size distribution is an advantage.

The cross-linking agent(s) is typically subsequently added to the emulsion, either directly or more typically by preparing a solution of the crosslinking agent in a solvent which is soluble in the continuous phase. The emulsion and cross-linking agent or solution hereof can be mixed by conventional methods used in the art, e.g., by simple mixing or by carefully controlling the flows of the emulsion and the cross-linking agent solution through an in-line mixer.

In some cases, curing of the capsules is needed to complete the membrane formation. Curing is often simple stirring of the capsules for some time to allow the interfacial polymerization reaction to end. In other cases the membrane formation can be stopped by addition of reaction quencher.

The capsules may be post modified, e.g., by reacting components onto the membrane to hinder or reduce flocculation of the particles in the detergent as described in WO 99/01534.

The produced capsules can be isolated or concentrated by methods known in the art, e.g., by filtration, centrifugation, distillation or decantation of the capsule dispersion.

The resulting capsules can be further formulated, e.g., by addition of surfactants to give the product the desired properties for storage, transport and later handling and addition to the detergent. Other microcapsule formulation agents include rheology modifiers, biocides (e.g., Proxel), acid/base for adjustment of pH (which will also adjust inside the microcapsules), and water for adjustment of water activity.

The capsule forming process may include the following steps:
Preparation of the initial water and oil phase(s),
Forming a water-in-oil emulsion,
Membrane formation by interfacial polymerization,
Optional post modification,
Optional isolation and/or formulation,
Addition to detergent.

The process can be either a batch process or a continuous or semi-continuous process.

A microcapsule may be a small aqueous sphere with a uniform membrane around it. The material inside the microcapsule is referred to as the core, internal phase, or fill, whereas the membrane is sometimes called a shell, coating, or wall. The microcapsules typically have diameters between 0.5 µm and 2 millimeters. Preferably, the mean diameter of the microcapsules is in the range of 1 µm to 1000 µm, more preferably in the range of 5 µm to 500 µm, even more preferably in the range of 10 µm to 500 µm, even more preferably in the range of 50 µm to 500 µm, and most preferably in the range of 50 µm to 200 µm. Alternatively, the diameter of the microcapsules is in the range of 0.5 µm to 30 µm; or in the range of 1 µm to 25 µm. The diameter of the microcapsule is measured in the oil phase after polymerization is complete. The diameter of the capsule may change depending on the water activity of the surrounding chemical environment.

Microencapsulation of enzymes may be carried out by interfacial polymerization, wherein the two reactants in a polymerization reaction meet at an interface and react rapidly. The basis of this method is a reaction of a polyamine with an acid derivative, usually an acid halide, acting as a crosslinking agent. The polyamine is preferably substantially water-soluble (when in free base form). Under the right conditions, thin flexible membranes form rapidly at the interface. One way of carrying out the polymerization is to use an aqueous solution of the enzyme and the polyamine, which are emulsified with a non-aqueous solvent (and an emulsifier), and a solution containing the acid derivative is added. An alkaline agent may be present in the enzyme solution to neutralize the acid formed during the reaction. Polymer (polyamide) membranes form instantly at the interface of the emulsion droplets. The polymer membrane of the microcapsule is typically of a cationic nature, and thus bind/complex with compounds of an anionic nature.

The diameter of the microcapsules is determined by the size of the emulsion droplets, which is controlled, for example by the stirring rate.

Emulsion: An emulsion is a temporary or permanent dispersion of one liquid phase within a second liquid phase. The second liquid is generally referred to as the continuous phase. Surfactants are commonly used to aid in the formation and stabilization of emulsions. Not all surfactants are equally able to stabilize an emulsion. The type and amount of a surfactant needs to be selected for optimum emulsion utility especially with regard to preparation and physical stability of the emulsion, and stability during dilution and further processing. Physical stability refers to maintaining an emulsion in a dispersion form. Processes such as coalescence, aggregation, adsorption to container walls, sedimentation and creaming, are forms of physical instability, and should be avoided. Examples of suitable surfactants are described in WO 97/24177, page 19-21; and in WO 99/01534.

Emulsions can be further classified as either simple emulsions, wherein the dispersed liquid phase is a simple homogeneous liquid, or a more complex emulsion, wherein the dispersed liquid phase is a heterogeneous combination of liquid or solid phases, such as a double emulsion or a multiple-emulsion. For example, a water-in-oil double emulsion or multiple emulsions may be formed wherein the water phase itself further contains an emulsified oil phase; this type of emulsion may be specified as an oil-in-water-in oil (o/w/o) emulsion. Alternatively, a water-in-oil emulsion may be formed wherein the water phase contains a dispersed solid phase often referred to as a suspension-emulsion. Other more complex emulsions can be described. Because of the inherent difficulty in describing such systems, the term emulsion is used to describe both simple and more complex emulsions without necessarily limiting the form of the emulsion or the type and number of phases present Polyamine: The rigidity/flexibility and permeability of the membrane is mainly influenced by the choice of polyamine. The polyamine according to the invention is a polybranched polyamine. Each branch, preferably ending with a primary amino group serves as a tethering point in the membrane network, thereby giving the favourable properties of the invention. A polybranched polyamine according to the present invention is a polyamine having more than two branching points and more than two reactive amino groups (capable of reacting with the crosslinking agent, i.e., primary and secondary amino groups). The polybranched polyamine is used as starting material when the emulsion is prepared— it is not formed in situ from other starting materials. To obtain the attractive properties, the polybranched structure of the polyamine must be present as starting material.

There is a close relation between number of branching points and number of primary amines, since primary amines will always be positioned at the end of a branch: A linear amine can only contain two primary amines. For each branching point hypothetically introduced in such a linear di-amine will allow one or more primary amine(s) to be introduced at the end of the introduced branch (es). In this context we the primary amino group is understood as part of the branch, i.e., the endpoint of the branch. For example, both tris(2-aminoethyl)amine and 1,2,3-propanetriamine is considered as molecules having one branching point. The polyamine preferably has at least four primary amines. Branching points can be introduced from an aliphatic hydrocarbon chain from unsaturated carbon bonds, such as in, e.g., 3,3'-diaminobenzidine, or from tertiary amino groups, such as in N,N,N',N'-tetrakis-(2-aminoethyl)ethylenediamine.

In addition to the number of branching points, the compactness of the reactive amino groups is of high importance. A substance such as, e.g., N,N,N',N'-tetrakis-(12-aminododecyl)ethylenediamine would not be suitable. Neither would a peptide or protein, such as an enzyme, be suitable for membrane formation. Thus, the polybranched polyamine is not a peptide or protein.

The reactive amino groups preferably constitute at least 15% of the molecular weight of the polybranched polyamine, such as more than 20%, or more than 25%. Preferably, the molecular weight of the polybranched polyamine is at least 1 kDa; more preferably, the molecular weight of the polybranched polyamine is at least 1.3 kDa.

The polybranched polyamine may be a polyethyleneimine (PEI), and modifications thereof, having more than two branching points and more than two reactive amino groups; wherein the reactive amino groups constitute at least 15% of the molecular weight of the PEI, such as more than 20%, or more than 25%. Preferably, the molecular weight of the PEI is at least 1 kDa.

Combinations of different polybranched polyamines may be used for preparing the microcapsule.

The advantageous properties (e.g., enzyme storage stability, reduced enzyme leakage, reduced in-flux of detergent ingredients) of the microcapsule may be improved by adding one or more small amines with a molecular weight of less than 1 kDa. The small amine is preferably substantially water-soluble (when in free base form) and can be a material such as ethylene diamine, hexamethylene diamine, hexane diamine, diethylene tetramine, ethylene tetramine, diamino benzene, piperazine, tetramethylene pentamine or, preferably, diethylene triamine (DETA). The small amines may be added in an amount of up to 50%, preferably up to 40%, up to 30%, up to 20%, up to 10%, or up to 5%, by weight of the total content of small amine and polybranched polyamine, when preparing the microcapsule.

Crosslinking agent: The crosslinking agent as used in the present invention is a molecule with at least two groups/sites capable of reacting with amines to form covalent bonds.

The crosslinking agent is preferably oil soluble and can be in the form of an acid anhydride or acid halide, preferably an acid chloride. For example, it can be adipoyl chloride, sebacoyl chloride, dodecanedioc acid chloride, phthaloyl chloride, terephthaloyl chloride, isophthaloyl chloride, or trimesoyl chloride; but preferably, the crosslinking agent is terephthaloyl chloride or trimesoyl chloride.

The liquid detergent composition may comprise a microcapsule, and thus form part of, any detergent composition in any form, such as liquid and powder detergents, and soap and detergent bars.

The microcapsule, as described above, may be added to the liquid detergent composition in an amount corresponding to from 0.0001% to 5% (w/w) active enzyme protein (AEP); preferably from 0.001% to 5%, more preferably from 0.005% to 5%, more preferably from 0.005% to 4%, more preferably from 0.005% to 3%, more preferably from 0.005% to 2%, even more preferably from 0.01% to 2%, and most preferably from 0.01% to 1% (w/w) active enzyme protein.

The liquid detergent composition has a physical form, which is not solid (or gas). It may be a pourable liquid, a paste, a pourable gel or a non-pourable gel. It may be isotropic or structured, preferably isotropic. It may be a formulation useful for washing in automatic washing machines or for hand washing. It may also be a personal care product, such as a shampoo, toothpaste, or hand soap.

The microcaplsule is further described in WO 2014/177709 which is incorporated by reference.

Formulation of Enzyme in Co-Granule

The DNase may be formulated as a granule for example as a co-granulate that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component. WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

Formulation of Detergent

Detergent ingredients can be separated physically from each other by compartments in water dissolvable pouches. Thereby negative storage interaction between components can be avoided. Different dissolution profiles of each of the compartments can also give rise to delayed dissolution of selected components in the wash solution.

The detergent composition may take the form of a unit dose product. A unit dose product is the packaging of a single dose in a non-reusable container. It is increasingly used in detergents for laundry. A detergent unit dose product is the packaging (e.g., in a pouch made from a water soluble film) of the amount of detergent used for a single wash.

Pouches can be of any form, shape and material which is suitable for holding the composition, e.g., without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be a blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticizers like glycerol, ethylene glycerol, Propylene glycol, sorbitol and mixtures thereof. The pouches can comprise a solid laundry detergent composition or part components and/or a liquid detergent composition or part components separated by the water soluble film. The compartment for liquid components can be different in composition than compartments containing solids (see e.g., US 2009/0011970).

Laundry Soap Bars

The DNase of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g. a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing soap, DNase, optionally one or more additional enzymes, a protease inhibitor, and a salt of a monovalent cation and an organic anion may be prepared and the mixture is then plodded. The DNase and optional additional enzymes may be added at the same time as the protease inhibitor for example in liquid form. Besides the mixing step and the plodding step, the process may further comprise the steps of milling, extruding, cutting, stamping, cooling and/or wrapping.

Pharmaceutical Compositions and Uses

The invention further concerns a pharmaceutical composition comprising one or more polypeptides according to the invention and a pharmaceutical adjunct ingredient, wherein the polypeptide having DNase activity. The adjunct ingredient may be any excipient suitable for pharmaceutical compositions. The adjunct/excipient are within the choice of the skilled artisan. The pharmaceutical composition further comprise a polypeptide selected from the group consisting of polypeptides comprising SEQ ID NOS 1, 2, 3, 4, 5, 6, 7, 8, 9, 10, 11, 12, 13, 14, 15, 16, 17, 18, 19 and 20, or DNases having at least 80% sequence identity hereto. The pharmaceutical compositions can be used for releasing or removing a biofilm or preventing biofilm formation on surfaces such as medical devices.

The use may be indwelling medical device characterised in that at least a portion of a patient-contactable surface of said device is coated with the pharmaceutical composition comprising the DNases of the invention.

The device can be a catheter such as a central venous catheter, intravascular catheter, urinary catheter, Hickman catheter, peritoneal dialysis catheter, endrotracheal catheter, or wherein the device is a mechanical heart valve, a cardiac pacemaker, an arteriovenous shunt, a scleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector or a surgical instrument. The pharmaceutical composition can be formulated as a liquid, lotion, cream, spray, gel or ointment. The pharmaceutical composition can be for administration to an animal patient. The animal patient can be a mammalian patient. The mammalian patient can be a human The invention is further summarized in the following paragraphs:

1. Use of a polypeptide having DNase activity, wherein the polypeptide is selected from the group consisting of SEQ ID NOS: 1, 2, 3, 4, 5, 6, 7, 8, 9, 10, 11, 12, 13, 14, 15, 16, 17, 18, 19 or 20 or a DNase having at least 80% sequence identity heretofore preventing, reducing or removing a biofilm from an item, wherein the item is a textile.
2. Use according to paragraph 1 for preventing, reducing or removing stickiness of the item.
3. Use according to any of paragraphs 1 or 2 for pretreating stains on the item.
4. Use according to any of paragraphs 1-3 for preventing, reducing or removing redeposition of soil during a wash cycle.
5. Use according to any of paragraphs 1-4 for preventing, reducing or removing adherence of soil to the item.
6. Use according to any of the preceding paragraphs for maintaining or improving the whiteness of the item.
7. Use according to any of the preceding paragraphs, wherein the polypeptide is the polypeptide of paragraphs 45-54.
8. Use according to any of the preceding paragraphs, wherein a malodor is reduced or removed from the item.
9. Use according to any of the preceding paragraphs, wherein the malodor is caused by E-2-nonenal.
10. Use according to any of the preceding paragraphs, wherein the amount of E-2-nonenal present on a wet textile is reduced or removed.
11. Use according to any of the preceding paragraphs, wherein the amount of E-2-nonenal present on a dry textile is reduced or removed.
12. A detergent composition comprising a polypeptide having deoxyribonuclease (DNase) activity selected from the group consisting of SEQ ID NOS: 1, 2, 3, 4, 5, 6, 7, 8, 9, 10, 11, 12, 13, 14, 15, 16, 17, 18, 19 and 20 or DNases having at least 80% sequence identity hereto and a detergent adjunct ingredient.
13. Detergent composition according to paragraph 12, wherein the polypeptide is obtained from *Paenibacillus* sp-62212, *Paenibacillus* sp-62605, *Bacillus* sp-62738, *Bacillus pumilus, Bacillus horikoshii, Bacillus* sp-62490, *Bacillus* sp-13390, *Jeotgalibacillus* sp-13376, *Bacillus* sp-62738, *Streptomyces iakyrus, Streptococcus infantis, Bacillus* sp-62599, *Bacillus akibai, Paenibacillus xylanexedens, Penicillium reticulisporum, Fictibacillus* sp-62719, *Bacillus algicola, Exiguobacterium* sp. NG55, Metagenome from environmental sample J, *Streptomyces thermoalcalitolerans* or Metagenome from environmental sample C.

14. Detergent composition according to any of the preceding composition paragraphs, wherein the polypeptides with SEQ ID NOS 1, 2, 3, 4, 5, 6, 7, 8, 9, 10, 11, 12, 13, 14, 15, 16, 17, 18, 19 or 20 are obtained from *Paenibacillus* sp-62212, *Paenibacillus* sp-62605, *Bacillus* sp-62738, *Bacillus pumilus, Bacillus horikoshii, Bacillus* sp-62490, *Bacillus* sp-13390, *Jeotgalibacillus* sp-13376, *Bacillus* sp-62738, *Streptomyces iakyrus, Streptococcus infantis, Bacillus* sp-62599, *Bacillus akibai, Paenibacillus xylanexedens, Penicillium reticulisporum, Fictibacillus* sp-62719, *Bacillus algicola, Exiguobacterium* sp. NG55, Metagenome from environmental sample J, *Streptomyces thermoalcalitolerans* or Metagenome from environmental sample C respectively.

15. Detergent composition according to any of the preceding paragraphs, wherein the polypeptide is the polypeptide of paragraphs 45-54.

16. Detergent composition according to any of the preceding composition paragraphs, wherein the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

17. Detergent composition according to any of the preceding composition paragraphs, wherein the composition further comprises one or more enzymes selected from the group consisting of proteases, lipases, cutinases, amylases, carbohydrases, cellulases, pectinases, mannanases, arabinases, galactanases, xylanases and oxidases.

18. Detergent composition according to any of the preceding composition paragraphs, wherein the enzyme is a protease, which is of animal, vegetable or microbial origin.

19. Detergent composition according to any of the preceding composition paragraphs, wherein the protease is chemically modified or protein engineered.

20. Detergent composition according to any of the preceding composition paragraphs, wherein the protease is a serine protease or a metalloprotease, preferably an alkaline microbial protease or a trypsin-like protease.

21. Detergent composition according to any of the preceding composition paragraphs, wherein the protease is selected from the group consisting of *Bacillus*, e.g., subtilisin Novo, subtilisin Carlsberg, subtilisin 309, subtilisin 147, subtilisin 168, trypsin of bovine origin, trypsin of porcine origin and *Fusarium* protease.

22. Detergent composition according to any of the preceding composition paragraphs, wherein the detergent composition is capable of reducing adhesion of bacteria selected from the group consisting of *Acinetobacter* sp., *Aeromicrobium* sp., *Brevundimonas* sp., *Microbacterium* sp., *Micrococcus luteus, Pseudomonas* sp., *Staphylococcus epidermidis*, and *Stenotrophomonas* sp. to a surface, or releasing the bacteria from a surface to which they adhere.

23. Detergent composition according to any of the preceding composition paragraphs, wherein the surface is a textile surface.

24. Detergent composition according to any of the preceding composition paragraphs, wherein the textile is made of cotton, Cotton/Polyester, Polyester, Polyamide, Polyacryl and/or silk.

25. Detergent composition according to any of the preceding composition paragraphs, wherein the composition is a bar, a homogenous tablet, a tablet having two or more layers, a pouch having one or more compartments, a regular or compact powder, a granule, a paste, a gel, or a regular, compact or concentrated liquid.

26. Detergent composition according to any of the preceding composition paragraphs, wherein the composition is a liquid detergent, a powder detergent or a granule detergent.

27. A laundering method for laundering an item comprising the steps of:
    a. Exposing an item to a wash liquor comprising a polypeptide of paragraphs 45-54 or a detergent composition according to any of paragraphs 12-26;
    b. Completing at least one wash cycle; and
    c. Optionally rinsing the item,
    wherein the item is a textile.

28. Method according to paragraph 27, wherein the pH of the wash liquor is in the range of 1 to 11.

29. Method according to any of the preceding method paragraphs, wherein the pH of the wash liquor is in the range 5.5 to 11, such as in the range of 7 to 9, in the range of 7 to 8 or in the range of 7 to 8.5.

30. Method according to any of the preceding method paragraphs, wherein the temperature of the wash liquor is in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C.

31. Method according to any of the preceding method paragraphs, wherein the temperature of the wash liquor is 30° C.

32. Method according to any of the preceding method paragraphs, wherein the method further comprises draining of the wash liquor or part of the wash liquor after completion of a wash cycle.

33. Method according to any of the preceding method paragraphs, wherein the item is exposed to the wash liquor during a first and optionally a second or a third wash cycle.

34. Method according to any of the preceding method paragraphs, wherein the item is rinsed after being exposed to the wash liquor.

35. Method according to any of the preceding method paragraphs, wherein the item is rinsed with water or with water comprising a conditioner.

36. Method according to any of the preceding method paragraphs, wherein stickiness of the item is reduced.

37. Method according to any of the preceding method paragraphs, wherein stains present on the item is pretreated with a polypeptide of paragraphs 45-54 or a detergent composition according to any of paragraphs 12-26.

38. Method according to any of the preceding method paragraphs, wherein redeposition of soil is reduced.

39. Method according to any of the preceding method paragraphs, wherein adherence of soil to the item is reduced or removed.

40. Method according to any of the preceding method paragraphs, wherein whiteness of the item is maintained or improved.

41. Method according to any of the preceding method paragraphs, wherein malodor is reduced or removed from the item.
42. Method according to any of the preceding method paragraphs, wherein the malodor is caused by E-2-nonenal.
43. Method according to any of the preceding method paragraphs, wherein the amount of E-2-nonenal present on a wet or dry textile is reduced or removed.
44. Method according to any of the preceding method paragraphs, wherein the concentration of the polypeptide in the wash liquor is at least 1 mg of DNase protein, such as at least 5 mg of protein, preferably at least 10 mg of protein, more preferably at least 15 mg of protein, even more preferably at least 20 mg of protein, most preferably at least 30 mg of protein, and even most preferably at least 40 mg of protein per liter of wash liquor.
45. A polypeptide having DNase activity, selected from the group consisting of:
   a. a polypeptide having at least 60% sequence identity to any of the polypeptides of SEQ ID NO: 1, 2, 3, 4, 5, 6, 7, 8, 9, 10, 11, 12, 13, 14, 15, 16, 17, 18, 19 or 20;
   b. a polypeptide encoded by a polynucleotide that hybridizes under low stringency conditions with
      i. the mature polypeptide coding sequence,
      ii. the full-length complement of (i);
   c. a variant of the mature polypeptide of SEQ ID NO: 1, 2, 3, 4, 5, 6, 7, 8, 9, 10, 11, 12, 13, 14, 15, 16, 17, 18, 19 or 20 comprising a substitution, deletion, and/or insertion at one or more positions; and
   d. a fragment of the polypeptide of (a), (b) or (c), that has DNase activity;
46. The polypeptide of paragraph 45, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to any of the polypeptides of SEQ ID NO: 1, 2, 3, 4, 5, 6, 7, 8, 9, 10, 11, 12, 13, 14, 15, 16, 17, 18, 19 or 20.
47. The polypeptide according to any of paragraphs 45-46, comprising or consisting of SEQ ID NO: 8, 9 or 10.
48. The polypeptide according to any of paragraphs 45-47, which is a variant of the polypeptide of SEQ ID NO: 1, 2, 3, 4, 5, 6, 7, 8, 9, 10, 11, 12, 13, 14, 15, 16, 17, 18, 19 or 20 comprising a substitution, deletion, and/or insertion at one or more positions.
49. The polypeptide according to paragraph 48, which is a fragment of SEQ ID NO: 1, 2, 3, 4, 5, 6, 7, 8, 9, 10, 11, 12, 13, 14, 15, 16, 17, 18, 19 or 20 wherein the fragment has DNase activity.
50. A polynucleotide encoding the polypeptide according to any of paragraphs 45-49.
51. A nucleic acid construct or expression vector comprising the polynucleotide of paragraph 50 operably linked to one or more control sequences that direct the production of the polypeptide in an expression host.
52. A recombinant host cell comprising the polynucleotide of paragraph 50-51 operably linked to one or more control sequences that direct the production of the polypeptide.
53. A method of producing the polypeptide of any of paragraphs 45-49, comprising cultivating a cell, which in its wild-type form produces the polypeptide, under conditions conducive for production of the polypeptide.
54. The method of paragraph 53, further comprising recovering the polypeptide.
55. A method of producing a polypeptide having DNase activity, comprising cultivating the host cell of paragraph 52 under conditions conducive for production of the polypeptide.
56. The method of paragraph 55, further comprising recovering the polypeptide.
57. A method of producing a protein, comprising cultivating the recombinant host cell comprising a gene encoding a protein operably linked to the polynucleotide of paragraph 50, wherein the gene is foreign to the polynucleotide encoding the propeptide, under conditions conducive for production of the protein.
58. The method of paragraph 57, further comprising recovering the protein.
59. A whole broth formulation or cell culture composition comprising a polypeptide of any of paragraphs 45-49.
60. An Item laundered according to the method of any of paragraphs 27-44.
61. A pharmaceutical composition comprising a polypeptide having DNase activity and a pharmaceutical adjunct ingredient, wherein the polypeptide is obtained from a bacterial source.
62. Pharmaceutical composition according to paragraph 61, wherein the polypeptide having DNase activity is obtained from *Bacillus, Streptomyces, Jeotgalibacillus, Fictibacillus, Penicillium, Exiguobacterium* or *Paenibacillus*.
63. Pharmaceutical composition according to any of paragraphs 61-62, wherein the polypeptide having DNase activity is obtained from *Paenibacillus* sp-62212, *Paenibacillus* sp-62605, *Bacillus* sp-62738, *Bacillus pumilus, Bacillus horikoshii, Bacillus* sp-62490, *Bacillus* sp-13390, *Jeotgalibacillus* sp-13376, *Bacillus* sp-62738, *Streptomyces iakyrus, Streptococcus infantis, Bacillus* sp-62599, *Bacillus akibai, Paenibacillus xylanexedens, Penicillium reticulisporum, Fictibacillus* sp-62719, *Bacillus algicola, Exiguobacterium* sp. NG55, Metagenome from environmental sample J, *Streptomyces thermoalcalitolerans* or Metagenome from environmental sample C
64. Pharmaceutical composition according to any of paragraphs 61-63, wherein the polypeptide is the polypeptide of paragraphs 45-49.
65. Pharmaceutical composition according to any of paragraphs 61-64, wherein the composition is formulated as a dental paste, a liquid dentifrice, a mouthwash, a troche or a gingival massage ointment.
66. Pharmaceutical composition according to any of paragraphs 61-65, further comprising one or more of an antimicrobial compound, such as an antibacterial compound, an antiparasitic compound, an antifungal compound and an antiviral compound.
67. An indwelling medical device characterised in that at least a portion of a patient-contactable surface of said device is coated with the pharmaceutical composition of any of paragraphs 61-66.
68. The device according to paragraph 67 wherein said device is a catheter such as a central venous catheter, intravascular catheter, urinary catheter, Hickman catheter, peritoneal dialysis catheter, endrotracheal catheter, or wherein the device is a mechanical heart valve, a cardiac pacemaker, an arteriovenous shunt, a schleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector or a surgical instrument.
69. A method of producing the polypeptide of any of paragraphs 45-49, comprising cultivating the host cell of paragraph 52 under conditions conducive for production of the polypeptide.
70. The method of paragraph 69, further comprising recovering the polypeptide.
71. The recombinant host cell of paragraph 52 further comprising a polynucleotide encoding a second polypeptide of interest; preferably an enzyme of interest; more preferably a secreted enzyme of interest; even more preferably a hydrolase, isomerase, ligase, lyase, oxidoreductase, or a transferase; and most preferably the secreted enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.
72. The recombinant host cell of paragraph 71, wherein the second polypeptide of interest is heterologous or homologous to the host cell.
73. The recombinant host cell of paragraph 71 or 72, which is a bacterial host cell; preferably a prokaryotic host cell; more preferably a Gram-positive host cell; even more preferably a *Bacillus, Clostridium, Enterococcus, Geobacillus, Lactobacillus, Lactococcus, Oceanobacillus, Staphylococcus, Streptococcus*, or *Streptomyces* host cell; and most preferably a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* host cell.
74. A method of producing the second polypeptide of interest as defined in any of paragraphs 69-70, comprising cultivating the host cell of any of paragraphs 71-73 under conditions conducive for production of the second polypeptide of interest.
75. The method of paragraph 74, further comprising recovering the second polypeptide of interest.
76. Detergent composition according to any of the preceding composition paragraphs, wherein the detergent adjunct ingredient is a surfactant.
77. Detergent composition according to any of the preceding composition paragraphs, wherein the detergent adjunct ingredient is a builder.
78. Detergent composition according to any of the preceding composition paragraphs, wherein the detergent adjunct ingredient is a clay soil removal/anti-redeposition agents.
79. Detergent composition according to paragraphs 12-26, wherein the composition is a liquid detergent composition, comprising a surfactant and a detergent builder in a total concentration of at least 3% by weight, and a detergent enzyme containing microcapsule, wherein the membrane of the microcapsule is produced by cross-linking of a polybranched polyamine having a molecular weight of more than 1 kDa.
80. Detergent composition according to paragraphs 79, wherein the reactive amino groups of the polybranched polyamine constitute at least 15% of the molecular weight.
81. Detergent composition according to any of paragraphs 79-80, wherein the microcapsule is produced by using an acid chloride as crosslinking agent.
82. Detergent composition according to any of paragraphs 79-81, wherein the diameter of the microcapsule is at least, or above, 50 micrometres.
83. Detergent composition according to any of paragraphs 79-82, wherein the microcapsule contains at least 1% by weight of active enzyme.
84. Detergent composition according to any of paragraphs 79-83, which further includes an alcohol, such as a polyol.
85. Detergent composition according to any of paragraphs 79-84, wherein the surfactant is an anionic surfactant.
86. Detergent composition according to any of paragraphs 79-85, which is a liquid laundry composition.
87. Detergent composition according to any of paragraphs 79-86, which contains less than 90% by weight of water.
88. Detergent composition according to any of paragraphs 79-87, wherein the detergent enzyme is a polypeptide having DNase activity, protease, amylase, lipase, cellulase, mannanase, pectinase, or oxidoreductase.
89. Detergent composition according to any of paragraphs 79-88, wherein the protease is a metalloprotease or an alkaline serine protease, such as a subtilisin.
90. Detergent composition according to any of paragraphs 79-89, wherein the polypeptide having DNase activity is the polypeptide according to any of paragraphs 45-49.
91. Detergent composition according to any of paragraphs 79-90, wherein the microcapsule is produced by interfacial polymerization using an acid chloride as crosslinking agent.
92. Detergent composition according to any of paragraphs 79-90, wherein the polybranched polyamine is a polyethyleneimine.
93. Detergent composition according to any of paragraphs 79-90, wherein the microcapsule comprises a source of Mg2+, Ca2+, or Zn2+ ions, such as a poorly soluble salt of Mg2+, Ca2+, or Zn2+.

Assays and Detergent Compositions
Detergent Compositions

The below mentioned detergent composition can be used in combination with the enzyme of the invention.
Biotex Black (Liquid)

5-15% Anionic surfactants, <5% Nonionic surfactants, perfume, enzymes, DMDM and hydantoin.
Composition of Ariel Sensitive White & Color, Liquid Detergent Composition Aqua, Alcohol Ethoxy Sulfate, Alcohol Ethoxylate, Amino Oxide, Citrid Acid, C12-18 topped palm kernel fatty acid, Protease, Glycosidase, Amylase, Ethanol, 1.2 Propanediol, Sodium Formate, Calcium Chloride, Sodium hydroxide, Silicone Emulsion, Trans-sulphated EHDQ (the ingredients are listed in descending order).
Composition of WFK IEC-A Model Detergent (Powder)

Ingredients: Linear sodium alkyl benzene sulfonate 8.8%, Ethoxylated fatty alcohol C12-18 (7 EO) 4.7%, Sodium soap 3.2%, Anti foam DC2-4248S 3.9%, Sodium aluminium silicate zeolite 4A 28.3%, Sodium carbonate 11.6%, Sodium salt of a copolymer from acrylic and maleic acid (Sokalan CP5) 2.4%, Sodium silicate 3.0%, Carboxymethylcellulose 1.2%, Dequest 2066 2.8%, Optical whitener 0.2%, Sodium sulfate 6.5%, Protease 0.4%.

Composition of Model Detergent A (Liquid)

Ingredients: 12% LAS, 11% AEO Biosoft N25-7 (NI), 7% AEOS (SLES), 6% MPG (monopropylene glycol), 3% ethanol, 3% TEA, 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w)

Composition of Ariel Actilift (Liquid)

Ingredients: 5-15% Anionic surfactants; <5% Non-ionic surfactants, Phosphonates, Soap; Enzymes, Optical brighteners, Benzisothiazolinone, Methylisothiazolinone, Perfumes, Alpha-isomethyl ionone, Citronellol, Geraniol, Linalool.

Composition of Ariel Actilift Colour&Style (Liquid)

Ingredients: 5-15% Anionic surfactants; <5% Non-ionic surfactants, Phosphonates, Soap; Enzymes, Perfumes, Benzisothiazolinone, Methylisothiazolinone, Alpha-isomethyl ionone, Butylphenyl methylpropional, Citronellol, Geraniol, Linalool.

Composition of Persil Small & Mighty (Liquid)

Ingredients: 15-30% Anionic surfactants, Non-ionic surfactants, 5-15% Soap, <5% Polycarboxylates, Perfume, Phosphates, Optical Brighteners Persil 2 in 1 with Comfort Passion Flower Powder Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15 Pareth-7, Stearic Acid, Parfum, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinyl-aminostilbenesulfonate, Sodium bicarbonate, Phenylpropyl Ethyl Methicone, Butylphenyl Methylpropional, Glyceryl Stearates, Calcium carbonate, Sodium Polyacrylate, Alpha-Isomethyl Ionone, Disodium Distyrylbiphenyl Disulfonate, Cellulose, Protease, Limonene, PEG-75, Titanium dioxide, Dextrin, Sucrose, Sodium Polyaryl Sulphonate, CI 12490, CI 45100, CI 42090, Sodium Thiosulfate, CI 61585.

Persil Biological Powder

Sucrose, Sorbitol, Aluminum Silicate, Polyoxymethylene Melamine, Sodium Polyaryl Sulphonate, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Biological Tablets

Sodium carbonate, Sodium Carbonate Peroxide, Sodium bicarbonate, Zeolite, Aqua, Sodium Silicate, Sodium Lauryl Sulfate, Cellulose, TAED, Sodium Dodecylbenzenesulfonate, Hemicellulose, Lignin, Lauryl Glucoside, Sodium Acrylic Acid/MA Copolymer, Bentonite, Sodium chloride, Parfum, Tetrasodium Etidronate, Sodium sulfate, Sodium Polyacrylate, Dimethicone, Disodium Anilinomorpholinotriazinylaminostilbenesulfonate, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, CI 12490, Sodium Polyaryl Sulphonate, Sodium Thiosulfate, Amylase, Kaolin, Persil Colour Care Biological Powder Subtilisin, Imidazolidinone, Hexyl Cinnamal, Sucrose, Sorbitol, Aluminum Silicate, Polyoxymethylene Melamine, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Colour Care Biological Tablets

Sodium bicarbonate, Sodium carbonate, Zeolite, Aqua, Sodium Silicate, Sodium Lauryl Sulfate, Cellulose Gum, Sodium Dodecylbenzenesulfonate, Lauryl Glucoside, Sodium chloride, Sodium Acrylic Acid/MA Copolymer, Parfum, Sodium Thioglycolate, PVP, Sodium sulfate, Tetrasodium Etidronate, Sodium Polyacrylate, Dimethicone, Bentonite, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, Sodium Thiosulfate, Amylase, CI 74160, Kaolin.

Persil Dual Action Capsules Bio

MEA-Dodecylbenzenesulfonate, MEA-Hydrogenated Cocoate, C12-15 Pareth-7, Dipropylene Glycol, Aqua, Tetrasodium Etidronate, Polyvinyl Alcohol, Glycerin, Aziridine, homopolymer ethoxylated, Propylene glycol, Parfum, Sodium Diethylenetriamine Pentamethylene Phosphonate, Sorbitol, MEA-Sulfate, Ethanolamine, Subtilisin, Glycol, Butylphenyl Methylpropional, Boronic acid, (4-formylphenyl), Hexyl Cinnamal, Limonene, Linalool, Disodium Distyrylbiphenyl Disulfonate, Alpha-Isomethyl Ionone, Geraniol, Amylase, Polymeric Blue Colourant, Polymeric Yellow Colourant, Talc, Sodium chloride, Benzisothiazolinone, Mannanase, Denatonium Benzoate.

Persil 2 in 1 with Comfort Sunshiny Days Powder

Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15 Pareth-7, Parfum, Stearic Acid, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinyl-aminostilbenesulfonate, Sodium bicarbonate, Phenylpropyl Ethyl Methicone, Butylphenyl Methylpropional, Glyceryl Stearates, Calcium carbonate, Sodium Polyacrylate, Geraniol, Disodium Distyrylbiphenyl Disulfonate, Cellulose, Protease, PEG-75, Titanium dioxide, Dextrin, Sucrose, Sodium Polyaryl Sulphonate, CI 12490, CI 45100, CI 42090, Sodium Thiosulfate, CI 61585.

Persil Small & Mighty 2in 1 with Comfort Sunshiny Days

Aqua, C12-15 Pareth-7, Sodium Dodecylbenzenesulfonate, Propylene glycol, Sodium Hydrogenated Cocoate, Triethanolamine, Glycerin, TEA-Hydrogenated Cocoate, Parfum, Sodium chloride, Polyquaternium-10, PVP, Polymeric Pink Colourant, Sodium sulfate, Disodium Distyrylbiphenyl Disulfonate, Butylphenyl Methylpropional, Styrene/Acrylates Copolymer, Hexyl Cinnamal, Citronellol, Eugenol, Polyvinyl Alcohol, Sodium acetate, Isopropyl alcohol, Polymeric Yellow Colourant, Sodium Lauryl Sulfate.

Persil Small & Mighty Bio

Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Disodium Distyrylbiphenyl Disulfonate, Butylphenyl Methylpropional, Styrene/Acrylates Copolymer, Citronellol, Sodium sulfate, Peptides, salts, sugars from fermentation (process), Subtilisin, Glycerin, Boronic acid, (4-formylphenyl), Geraniol, Pectate Lyase, Amylase, Sodium Lauryl Sulfate, Mannanase, CI 42051.

Persil Small & Mighty Capsules Biological

MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, Sorbitol, MEA-Sulfate, Ethanolamine, Subtilisin, Glycol, Butylphenyl Methylpropional, Hexyl Cinnamal, Starch, Boronic acid, (4-formylphenyl), Limonene, Linalool, Disodium Distyrylbiphenyl Disulfonate, Alpha-Isomethyl Ionone, Geraniol, Amylase, Talc, Polymeric Blue Colourant, Sodium chloride, Benzisothiazolinone, Denatonium Benzoate, Polymeric Yellow Colourant, Mannanase.

Persil Small & Mighty Capsules Colour Care

MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, MEA-Sulfate, Ethanolamine, PVP, Sorbitol, Butylphenyl Methylpropional, Subtilisin, Hexyl Cinnamal, Starch, Limonene, Linalool, Boronic acid, (4-formylphenyl), Alpha-Isomethyl Ionone, Geraniol, Talc, Polymeric Blue Colourant, Denatonium Benzoate, Polymeric Yellow Colourant.

Persil Small & Mighty Colour Care

Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Glycerin, Butylphenyl Methylpropional, Citronellol, Sodium sulfate, Peptides, salts, sugars from fermentation (process), Styrene/Acrylates Copolymer, Subtilisin, Boronic acid, (4-formylphenyl), Geraniol, Pectate Lyase, Amylase, Sodium Lauryl Sulfate, Mannanase, CI 61585, CI 45100.

Composition of Fairy Non Bio (Liquid)

Ingredients: 15-30% Anionic Surfactants, 5-15% Non-Ionic Surfactants, Soap, Benzisothiazolinone, Methylisothiazolinone, Perfumes Composition of Model Detergent T (Powder)

Ingredients: 11% LAS, 2% AS/AEOS, 2% soap, 3% AEO, 15.15% sodium carbonate, 3% sodium slilcate, 18.75% zeolite, 0.15% chelant, 2% sodium citrate, 1.65% AA/MA copolymer, 2.5% CMC and 0.5% SRP (all percentages are w/w).

Composition of Model Detergent X (Powder)

Ingredients: 16.5% LAS, 15% zeolite, 12% sodium disilicate, 20% sodium carbonate, 1% sokalan, 35.5% sodium sulfate (all percentages are w/w).

Composition of Ariel Actilift Colour&Style (Powder)

Ingredients: 15-30% Anionic surfactants, <5% Non-ionic surfactants, Phosphonates, Polycarboxylates, Zeolites; Enzymes, Perfumes, Hexyl cinnamal.

Composition of Ariel Actilift (Powder)

Ingredients: 5-15% Anionic surfactants, Oxygen-based bleaching agents, <5% Non-ionic surfactants, Phosphonates, Polycarboxylates, Zeolites, Optical brighteners, Enzymes, Perfumes, Butylphenyl Methylpropional, Coumarin, Hexyl Cinnamal Composition of Persil Megaperls (Powder)

Ingredients: 15-30% of the following: anionic surfactants, oxygen-based bleaching agent and zeolites, less than 5% of the following: non-ionic surfactants, phosphonates, polycarboxylates, soap. Further ingredients: Perfumes, Hexyl cinnamal, Benzyl salicylate, Linalool, optical brighteners, Enzymes and Citronellol.

Gain Liquid, Original:

Ingredients: Water, Alcohol Ethoxysulfate, Diethylene Glycol, Alcohol Ethoxylate, Ethanolamine, Linear Alkyl Benzene Sulfonate, Sodium Fatty Acids, Polyethyleneimine Ethoxylate, Citric Acid, Borax, Sodium Cumene Sulfonate, Propylene Glycol, DTPA, Disodium Diaminostilbene Disulfonate, Dipropylethyl Tetraamine, Sodium Hydroxide, Sodium Formate, Calcium Formate, Dimethicone, Amylase, Protease, Liquitint™, Hydrogenated Castor Oil, Fragrance Tide Liquid, Original:

Ingredients: Linear alkylbenzene sulfonate, propylene glycol, citric acid, sodium hydroxide, borax, ethanolamine, ethanol, alcohol sulfate, polyethyleneimine ethoxylate, sodium fatty acids, diquaternium ethoxysulfate, protease, diethylene glycol, laureth-9, alkyldimethylamine oxide, fragrance, amylase, disodium diaminostilbene disulfonate, DTPA, sodium formate, calcium formate, polyethylene glycol 4000, mannanase, Liquitint™ Blue, dimethicone.

Liquid Tide, Free and Gentle:

Water, sodium alcoholethoxy sulfate, propylene glycol, borax, ethanol, linear alkylbenzene sulfonate sodium, salt, polyethyleneimine ethoxylate, diethylene glycol, trans sulfated & ethoxylated hexamethylene diamine, alcohol ethoxylate, linear alkylbenzene sulfonate, MEA salt, sodium formate, sodium alkyl sulfate, DTPA, amine oxide, calcium formate, disodium diaminostilbene, disulfonate, amylase, protease, dimethicone, benzisothiazolinone Tide Coldwater Liquid, Fresh Scent:

Water, alcoholethoxy sulfate, linear alkylbenzene sulfonate, diethylene glycol, propylene glycol, ethanolamine, citric acid, Borax, alcohol sulfate, sodium hydroxide, polyethyleneimine, ethoxylate, sodium fatty acids, ethanol, protease, Laureth-9, diquaternium ethoxysulfate, lauramine oxide, sodium cumene, sulfonate, fragrance, DTPA, amylase, disodium, diaminostilbene, disulfonate, sodium formate, disodium distyrylbiphenyl disulfonate, calcium formate, polyethylene glycol 4000, mannanase, pectinase, Liquitint™ Blue, dimethicone Tide TOTALCARE™ Liquid, Cool Cotton:

Water, alcoholethoxy sulfate, propylene glycol, sodium fatty acids, laurtrimonium chloride, ethanol, sodium hydroxide, sodium cumene sulfonate, citric acid, ethanolamine, diethylene glycol, silicone polyether, borax, fragrance, polyethyleneimine ethoxylate, protease, Laureth-9, DTPA, polyacrylamide quaternium chloride, disodium diaminostilbene disulfonate, sodium formate, Liquitint™ Orange, dipropylethyl tetraamine, dimethicone, cellulase, Liquid Tide Plus Bleach Alternative™, Vivid White and Bright, Original and Clean Breeze:

Water, sodium alcoholethoxy sulfate, sodium alkyl sulfate, MEA citrate, linear alkylbenzene sulfonate, MEA salt, propylene glycol, diethylene glycol, polyethyleneimine ethoxylate, ethanol, sodium fatty acids, ethanolamine, lauramine oxide, borax, Laureth-9, DTPA, sodium cumene sulfonate, sodium formate, calcium formate, linear alkylbenzene sulfonate, sodium salt, alcohol sulfate, sodium hydroxide, diquaternium ethoxysulfate, fragrance, amylase, protease, mannanase, pectinase, disodium diaminostilbene disulfonate, benzisothiazolinone, Liquitint™ Blue, dimethicone, dipropylethyl tetraamine.

Liquid Tide HE, Original Scent:

Water, Sodium alcoholethoxy sulfate, MEA citrate, Sodium Alkyl Sulfate, alcohol ethoxylate, linear alkylbenzene sulfonate, MEA salt, sodium fatty acids, polyethyleneimine ethoxylate, diethylene glycol, propylene glycol, diquaternium ethoxysulfate, borax, polyethyleneimine, ethoxylate propoxylate, ethanol, sodium cumene sulfonate, fragrance, DTPA, disodium diaminostilbene disulfonate, Mannanase, cellulase, amylase, sodium formate, calcium formate, Lauramine oxide, Liquitint™ Blue, Dimethicone/polydimethyl silicone.

Tide TOTALCARE HE Liquid, Renewing Rain:

Water, alcoholethoxy sulfate, linear alkylbenzene sulfonate, alcohol ethoxylate, citric acid, Ethanolamine, sodium fatty acids, diethylene glycol, propylene glycol, sodium hydroxide, borax, polyethyleneimine ethoxylate, silicone polyether, ethanol, protease, sodium cumene sulfonate, diquaternium ethoxysulfate, Laureth-9, fragrance, amylase, DTPA, disodium diaminostilbene disulfonate, disodium distyrylbiphenyl disulfonate, sodium formate, calcium formate, mannanase, Liquitint™ Orange, dimethicone, polyacrylamide quaternium chloride, cellulase, dipropylethyl tetraamine.

Tide Liquid HE Free:
  Water, alcoholethoxy sulfate, diethylene glycol, monoethanolamine citrate, sodium formate, propylene glycol, linear alkylbenzene sulfonates, ethanolamine, ethanol, polyethyleneimine ethoxylate, amylase, benzisothiazolin, borax, calcium formate, citric acid, diethylenetriamine pentaacetate sodium, dimethicone, diquaternium ethoxysulfate, disodium diaminostilbene disulfonate, Laureth-9, mannanase, protease, sodium cumene sulfonate, sodium fatty acids.

Tide Coldwater HE Liquid, Fresh Scent:
  Water, alcoholethoxy sulfate, MEA Citrate, alcohol sulfate, Alcohol ethoxylate, Linear alkylbenzene sulfonate MEA, sodium fatty acids, polyethyleneimine ethoxylate, diethylene glycol, propylene glycol, diquaternium ethoxysulfate, borax, polyethyleneimine ethoxylate propoxylate, ethanol, sodium cumene sulfonate, fragrance, DTPA, disodium diaminostilbene disulfonate, protease, mannanase, cellulase, amylase, sodium formate, calcium formate, lauramine oxide, Liquitint™ Blue, dimethicone.

Tide for Coldwater HE Free Liquid:
  Water, sodium alcoholethoxy sulfate, MEA Citrate, Linear alkylbenzene sulfonate: sodium salt, Alcohol ethoxylate, Linear alkylbenzene sulfonate: MEA salt, sodium fatty acids, polyethyleneimine ethoxylate, diethylene glycol, propylene glycol, diquaternium ethoxysulfate, Borax, protease, polyethyleneimine ethoxylate propoxylate, ethanol, sodium cumene sulfonate, Amylase, citric acid, DTPA, disodium diaminostilbene disulfonate, sodium formate, calcium formate, dimethicone.

Tide Simply Clean & Fresh:
  Water, alcohol ethoxylate sulfate, linear alkylbenzene sulfonate Sodium/Mea salts, propylene glycol, diethylene glycol, sodium formate, ethanol, borax, sodium fatty acids, fragrance, lauramine oxide, DTPA, Polyethylene amine ethoxylate, calcium formate, disodium diaminostilbene disulfonate, dimethicone, tetramine, Liquitint™ Blue.

Tide Pods, Ocean Mist, Mystic Forest, Spring Meadow:
  Linear alkylbenzene sulfonates, C12-16 Pareth-9, propylene glycol, alcoholethoxy sulfate, water, polyethyleneimine ethoxylate, glycerine, fatty acid salts, PEG-136 polyvinyl acetate, ethylene Diamine disuccinic salt, monoethanolamine citrate, sodium bisulfite, diethylenetriamine pentaacetate sodium, disodium distyrylbiphenyl disulfonate, calcium formate, mannanase, exyloglucanase, sodium formate, hydrogenated castor oil, natalase, dyes, termamyl, subtilisin, benzisothiazolin, perfume.

Tide to Go:
  Deionized water, Dipropylene Glycol Butyl Ether, Sodium Alkyl Sulfate, Hydrogen Peroxide, Ethanol, Magnesium Sulfate, Alkyl Dimethyl Amine Oxide, Citric Acid, Sodium Hydroxide, Trimethoxy Benzoic Acid, Fragrance.

Tide Stain Release Liquid:
  Water, Alkyl Ethoxylate, Linear Alkylbenzenesulfonate, Hydrogen Peroxide, Diquaternium Ethoxysulfate, Ethanolamine, Disodium Distyrylbiphenyl Disulfonate, tetrabutyl Ethylidinebisphenol, F&DC Yellow 3, Fragrance.

Tide Stain Release Powder:
  Sodium percarbonate, sodium sulfate, sodium carbonate, sodium aluminosilicate, nonanoyloxy benzene sulfonate, sodium polyacrylate, water, sodium alkylbenzenesulfonate, DTPA, polyethylene glycol, sodium palmitate, amylase, protease, modified starch, FD&C Blue 1, fragrance.

Tide Stain Release, Pre Treater Spray:
  Water, Alkyl Ethoxylate, MEA Borate, Linear Alkylbenzenesulfonate, Propylene Glycol, Diquaternium Ethoxysulfate, Calcium Chlorideenzyme, Protease, Ethanolamine, Benzoisothiazolinone, Amylase, Sodium Citrate, Sodium Hydroxide, Fragrance.

Tide to Go Stain Eraser:
  Water, Alkyl Amine Oxide, Dipropylene Glycol Phenyl Ether, Hydrogen Peroxide, Citric Acid, Ethylene Diamine Disuccinic Acid Sodium salt, Sodium Alkyl Sulfate, Fragrance.

Tide Boost with Oxi:
  Sodium bicarbonate, sodium carbonate, sodium percarbonate, alcohol ethoxylate, sodium chloride, maleic/acrylic copolymer, nonanoyloxy benzene sulfonate, sodium sulfate, colorant, diethylenetriamine pentaacetate sodium salt, hydrated aluminosilicate (zeolite), polyethylene glycol, sodium alkylbenzene sulfonate, sodium palmitate, starch, water, fragrance.

Tide Stain Release Boost Duo Pac:
  Polyvinyl Alcoholpouch film, wherein there is packed a liquid part and a powder part: Liquid Ingredients: Dipropylene Glycol, diquaternium Ethoxysulfate, Water, Glycerin, Liquitint™ Orange, Powder Ingredients: sodium percarbonate, nonanoyloxy benzene sulfonate, sodium carbonate, sodium sulfate, sodium aluminosilicate, sodium polyacrylate, sodium alkylbenzenesulfonate, maleic/acrylic copolymer, water, amylase, polyethylene glycol, sodium palmitate, modified starch, protease, glycerine, DTPA, fragrance.

Tide Ultra Stain Release:
  Water, sodium alcoholethoxy sulfate, linear alkyl benzene sulfonate, sodium/MEA salts, MEA citrate, propylene glycol, polyethyleneimine ethoxylate, ethanol, diethylene glycol, polyethyleneimine propoxyethoxylate, sodium fatty acids, protease, borax, sodium cumene sulfonate, DTPA, fragrance, amylase, disodium diaminostilbene disulfonate, calcium formate, sodium formate, gluconase, dimethicone, Liquitint™ Blue, mannanase.

Ultra Tide with a Touch of Downy® Powdered Detergent, April Fresh/Clean Breeze/April Essence:
  Sodium Carbonate, Sodium Aluminosilicate, Sodium Sulfate, Linear Alkylbenzene Sulfonate, Bentonite, Water, Sodium Percarbonate, Sodium Polyacrylate, Silicate, Alkyl Sulfate, Nonanoyloxybenzenesulfonate, DTPA, Polyethylene Glycol 4000, Silicone, Ethoxylate, fragrance, Polyethylene Oxide, Palmitic Acid, Disodium Diaminostilbene Disulfonate, Protease, Liquitint™ Red, FD&C Blue 1, Cellulase.

Ultra Tide with a Touch of Downy Clean Breeze:
  Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimine, propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, sodium formate, Liquitint™ Blue.

Ultra Tide with Downy Sun Blossom:
  Water, sodium alcoholethoxy sulfate, MEA citrate, linear alkyl benzene sulfonate: sodium/MEA salts, propylene glycol, ethanol, diethylene glycol, polyethyleneimine propoxyethoxylate, polyethyleneimine ethoxylate, alcohol sulfate, dimethicone, fragrance, borax, sodium fatty acids, DTPA, protease, sodium bisulfite, disodium diaminostilbene disulfonate, amylase, castor oil, calcium formate, MEA, styrene acrylate copolymer, propanaminium propanamide, gluconase, sodium formate, Liquitint™ Blue.

Ultra Tide with Downy April Fresh/Sweet Dreams:

Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimin propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, propanaminium propanamide, sodium formate, Liquitint™ Blue.

Ultra Tide Free Powdered Detergent:

Sodium Carbonate, Sodium Aluminosilicate, Alkyl Sulfate, Sodium Sulfate, Linear Alkylbenzene Sulfonate, Water, Sodium polyacrylate, Silicate, Ethoxylate, Sodium percarbonate, Polyethylene Glycol 4000, Protease, Disodium Diaminostilbene Disulfonate, Silicone, Cellulase.

Ultra Tide Powdered Detergent, Clean Breeze/Spring Lavender/Mountain Spring:

Sodium Carbonate, Sodium Aluminosilicate, Sodium Sulfate, Linear Alkylbenzene Sulfonate, Alkyl Sulfate, Sodium Percarbonate, Water, Sodium Polyacrylate, Silicate, Nonanoyloxybenzenesulfonate, Ethoxylate, Polyethylene Glycol 4000, Fragrance, DTPA, Disodium Diaminostilbene Disulfonate, Palmitic Acid, Protease, Silicone, Cellulase.

Ultra Tide HE (High Efficiency) Powdered Detergent, Clean Breeze:

Sodium Carbonate, Sodium Aluminosilicate, Sodium Sulfate, Linear Alkylbenzene Sulfonate, Water, Nonanoyloxybenzenesulfonate, Alkyl Sulfate, Sodium Polyacrylate, Silicate, Sodium Percarbonate, Ethoxylate, Polyethylene Glycol 4000, Fragrance, DTPA, Palmitic Acid, Disodium Diaminostilbene Disulfonate, Protease, Silicone, Cellulase.

Ultra Tide Coldwater Powdered Detergent, Fresh Scent:

Sodium Carbonate, Sodium Aluminosilicate, Sodium Sulfate, Sodium Percarbonate, Alkyl Sulfate, Linear Alkylbenzene Sulfonate, Water, Nonanoyloxybenzenesulfonate, Sodium Polyacrylate, Silicate, Ethoxylate, Polyethylene Glycol 4000, DTPA, Fragrance, Natalase, Palmitic Acid, Protease, Disodium, Diaminostilbene Disulfonate, FD&C Blue 1, Silicone, Cellulase, Alkyl Ether Sulfate.

Ultra Tide with Bleach Powdered Detergent, Clean Breeze:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate, Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

Ultra Tide with Febreeze Freshness™ Powdered Detergent, Spring Renewal:

Sodium Carbonate, Sodium Aluminosilicate, Sodium Sulfate, Linear Alkylbenzene Sulfonate, Sodium Percarbonate, Alkyl Sulfate, Water, Sodium Polyacrylate, Silicate, Nonanoyloxybenzenesulfonate, Ethoxylate, Polyethylene Glycol 4000, DTPA, Fragrance, Cellulase, Protease, Disodium Diaminostilbene Disulfonate, Silicone, FD&C Blue 1.

Liquid Tide Plus with Febreeze Freshness—Sport HE Active Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, Ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Plus Febreeze Freshness Spring & Renewal:

Water, sodium alcoholethoxy sulfate, linear alkyl benzene sulfonate: sodium/MEA salts, MEA citrate, propylene glycol, polyethyleneimine ethoxylate, fragrance, ethanol, diethylene glycol, polyethyleneimine propoxyethoxylate, protease, alcohol sulfate, borax, sodium fatty acids, DTPA, disodium diaminostilbene disulfonate, MEA, mannanase, gluconase, sodium formate, dimethicone, Liquitint™ Blue, tetramine.

Liquid Tide Plus with Febreeze Freshness, Sport HE Victory Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Vivid White+Bright Powder, Original:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

HEY SPORT TEX WASH Detergent

Aqua, dodecylbenzenesulfonsaure, laureth-11, peg-75 lanolin, propylene glycol, alcohol denat., potassium soyate, potassium hydroxide, disodium cocoamphodiacetate, ethylendiamine triacetate cocosalkyl acetamide, parfum, zinc ricinoleate, sodium chloride, benzisothiazolinone, methylisothiazolinone, ci 16255, benzyl alcohol.

The products named Tide, Ariel, Gain and Fairy are commercially available products supplied by Procter & Gamble. The products named Persil are commercially available products supplied by Unilever and Henkel. The products named Hey Sport are commercially available products supplied by Hey Sport.

| Ingredient | Amount (in wt %) |
|---|---|
| Anionic detersive surfactant (such as alkyl benzene sulphonate, alkyl ethoxylated sulphate and mixtures | from 8 wt % to 15 wt % thereof) |
| Non-ionic detersive surfactant (such as alkyl ethoxylated alcohol) | from 0.5 wt % to 4 wt % |

-continued

| Ingredient | Amount (in wt %) |
|---|---|
| Cationic detersive surfactant (such as quaternary ammonium compounds) | from 0 to 4 wt % |
| Other detersive surfactant (such as zwiterionic detersive surfactants, amphoteric surfactants and mixtures thereof) | from 0 wt % to 4 wt % |
| Carboxylate polymer (such as co-polymers of maleic acid and acrylic acid) | from 1 wt % to 4 wt % |
| Polyethylene glycol polymer (such as a polyethylene glycol polymer comprising poly vinyl acetate side chains) | from 0.5 wt % to 4 wt % |
| Polyester soil release polymer (such as Repel-o-tex from and/or Texcare polymers) | 0.1 to 2 wt % |
| Cellulosic polymer (such as carboxymethyl cellulose, methyl cellulose and combinations thereof) | from 0.5 wt % to 2 wt % |
| Other polymer (such as amine polymers, dye transfer inhibitor polymers, hexamethylenediamine derivative polymers, and mixtures thereof) | from 0 wt % to 4 wt % |
| Zeolite builder and phosphate builder (such as zeolite 4A and/or sodium tripolyphosphate) | from 0 wt % to 4 wt % |
| Other builder (such as sodium citrate and/or citric acid) | from 0 wt % to 3 wt % |
| Carbonate salt (such as sodium carbonate and/or sodium bicarbonate) | from 15 wt % to 30 wt % |
| Silicate salt (such as sodium silicate) | from 0 wt % to 10 wt % |
| Filler (such as sodium sulphate and/or bio-fillers) | from 10 wt % to 40 wt % |
| Source of available oxygen (such as sodium percarbonate) | from 10 wt % to 20 wt % |
| Bleach activator (such as tetraacetylethylene diamine (TAED) and/or nonanoyloxybenzenesulphonate (NOBS) | from 2 wt % to 8 wt % |
| Bleach catalyst (such as oxaziridinium-based bleach catalyst and/or transition metal bleach catalyst) | from 0 wt % to 0.1 wt % |
| Other bleach (such as reducing bleach and/or pre-formed peracid) | from 0 wt % to 10 wt % |
| Chelant (such as ethylenediamine-N'N'-disuccinic acid (EDDS) and/or hydroxyethane diphosphonic acid(HEDP) | from 0.2 wt % to 1 wt % |
| Photobleach (such as zinc and/or aluminium sulphonated phthalocyanine) | from 0 wt % to 0.1 wt % |
| Hueing agent (such as direct violet 99, acid red 52, acid blue 80, direct violet 9, solvent violet 13 and any combination thereof) | from 0 wt % to 1 wt % |
| Brightener (such as brightener 15 and/or brightener 49) | from 0.1 wt % to 0.4 wt % |
| Protease (such as Savinase, Savinase Ultra, Purafect, FN3, FN4 and any combination thereof) | from 0.1 wt % to 0.4 wt % |
| Amylase (such as Termamyl, Termamyl ultra Natalase, Optisize, Stainzyme, Stainzyme Plus, and any combination thereof) | from 0.05 wt % to 0.2 wt % |
| Cellulase (such as Carezyme and/or Celluclean) | from 0.05 wt % to 0.2 wt % |
| Lipase (such as Lipex, Lipolex, Lipoclean and any combination thereof) | from 0.2 to 1 wt % |
| Other enzyme (such as xyloglucanase, cutinase, pectate lyase, mannanase, bleaching enzyme) | from 0 wt % to 2 wt % |
| Fabric softener (such as montmorillonite clay and/or polydimethylsiloxane (PDMS) | from 0 wt % to 4 wt % |
| Flocculant (such as polyethylene oxide) | from 0 wt % to 1 wt % |
| Suds suppressor (such as silicone and/or fatty acid) | from 0 wt % to 0.1 wt % |
| Perfume (such as perfume microcapsule, spray-on perfume, starch encapsulated perfume accords, perfume loaded zeolite, and any combination thereof) | from 0.1 wt % to 1 wt % |
| Aesthetics (such as coloured soap rings and/or coloured speckles/noodles) | from 0 wt % to 1 wt % |
| Miscellaneous | Balance |

| Ingredient | Amount |
|---|---|
| Carboxyl group-containing polymer (comprising from about 60% to about 70% by mass of an acrylic acid-based monomer (A); and from about 30% to about 40%) by mass of a sulfonic acid group-containing monomer (B); and wherein the average molecular weight is from about 23,000 to about 50,000 preferably in the range of from about 25,000 to about 38,000 as described in WO2014032269. | from about 0.5 wt % to about 1.5 wt % |
| Amylase (Stainzyme Plus(R), having an enzyme activity of 14 mg active enzyme/g) | from about 0.1 wt % to about 0.5 wt % |
| Anionic detersive surfactant (such as alkyl benzene sulphonate, alkyl ethoxylated sulphate and mixtures thereof) | from about 8 wt % to about 15 wt % |
| Non-ionic detersive surfactant (such as alkyl ethoxylated alcohol) | from about 0.5 wt % to about 4 wt % |
| Cationic detersive surfactant (such as quaternary ammonium compounds) | from about 0 wt % to about 4 wt % |
| Other detersive surfactant (such as zwiterionic detersive surfactants, amphoteric surfactants and mixtures thereof) | from about 0 wt % to 4 wt % |

| Ingredient | Amount |
|---|---|
| Carboxylate polymer (such as co-polymers of maleic acid and acrylic acid) | from about 1 wt % to about 4 wt % |
| Polyethylene glycol polymer (such as a polyethylene glycol polymer comprising poly vinyl acetate side chains) | from about 0 wt % to about 4 wt % |
| Polyester soil release polymer (such as Repel-O-Tex(R) and/or Texcare(R) polymers) | from about 0.1 wt % to about 2 wt % |
| Cellulosic polymer (such as carboxymethyl cellulose, methyl cellulose and combinations thereof) | from about 0.5 wt % to about 2 wt % |
| Other polymer (such as amine polymers, dye transfer inhibitor polymers, hexamethylenediamine derivative polymers, and mixtures thereof) | from about 0 wt % to about 4 wt % |
| Zeolite builder and phosphate builder (such as zeolite 4A and/or sodium tripolyphosphate) | from about 0 wt % to about 4 wt % |
| Other builder (such as sodium citrate and/or citric acid) | from about 0 wt % to about 3 wt % |
| Carbonate salt (such as sodium carbonate and/or sodium bicarbonate) | from about 15 t % to about 30 wt % |
| Silicate salt (such as sodium silicate) | from about 0 wt % to about 10 wt % |
| Filler (such as sodium sulphate and/or bio-fillers) | from about 10 wt % to about 40 wt % |
| Source of available oxygen (such as sodium percarbonate) | from about 10 wt % to about 20 wt % |
| Bleach activator (such as tetraacetylethylene diamine (TAED) and/or nonanoyloxybenzenesulphonate (NOBS) | from about 2 wt % to about 8 wt % |
| Bleach catalyst (such as oxaziridinium-based bleach catalyst and/or transition metal bleach catalyst) | from about 0 wt % to about 0.1 wt % |
| Other bleach (such as reducing bleach and/or pre formed peracid) | from about 0 wt % to about 10 wt % |
| Chelant (such as ethylenediamine-N'N'-disuccinic acid (EDDS) and/or hydroxyethane diphosphonic acid (HEDP) | from about 0.2 wt % to about 1 wt % |
| Photobleach (such as zinc and/or aluminium sulphonated phthalocyanine) | from about 0 wt % to about 0.1 wt % |
| Hueing agent (such as direct violet 99, acid red 52, acid blue 80, direct violet 9, solvent violet 13 and any combination thereof) | from about 0 wt % to about 0.5 wt % |
| Brightener (such as brightener 15 and/or brightener 49) | from about 0.1 wt % to about 0.4 wt % |
| Protease (such as Savinase, Polarzyme, Purafect, FN3, FN4 and any combination thereof, typically having an enzyme activity of from about 20 mg to about 100 mg active enzyme/g) | from about 0.1 wt % to about 1.5 wt % |
| Amylase (such as Termamyl(R), Termamyl Ultra(R), Natalase(R), Optisize HT Plus(R), Powerase(R), Stainzyme(R) and any combination thereof, typically having an enzyme activity of from about 10 mg to about 50 mg active enzyme/g) | from about 0.05 wt % to about 0.2 wt % |
| Cellulase (such as Carezyme(R), Celluzyme(R) and/or Celluclean(R), typically having an enzyme activity of about from 10 to 50 mg active enzyme/g) | from about 0.05 wt % to 0.5 wt % |
| Lipase (such as Lipex(R), Lipolex(R), Lipoclean(R) and any combination thereof, typically having an enzyme activity of from about 10 mg to about 50 mg active enzyme/g) | from about 0.2 wt % to about 1 wt % |
| Other enzyme (such as xyloglucanase (e.g., Whitezyme(R)), cutinase, pectate lyase, mannanase, bleaching enzyme, typically having an enzyme activity of from about 10 mg to about 50 mg active enzyme/g) | from 0 wt % to 2 wt % |
| Fabric softener (such as montmorillonite clay and/or polydimethylsiloxane (PDMS)) | from 0 wt % to 15 wt % |
| Flocculant (such as polyethylene oxide) | from 0 wt % to 1 wt % |
| Suds suppressor (such as silicone and/or fatty acid) | from 0 wt % to 0.1 wt % |
| Perfume (such as perfume microcapsule, spray-on perfume, starch encapsulated perfume accords, perfume loaded zeolite, and any combination thereof) | from 0.1 wt % to 1 wt % |
| Aesthetics (such as colored soap rings and/or colored speckles/noodles) | from 0 wt % to 1 wt % |
| Miscellaneous | Balance |

All enzyme levels expressed as rug active enzyme protein per 100 g detergent composition. Surfactant ingredients can be obtained from BASF, Ludwigshafen, Germany (Lutensol(R)); Shell Chemicals, London, UK; Stepan, Northfield, Ill., USA; Huntsman, Huntsman, Salt Lake City, Utah, USA; Clariant, Sulzbach, Germany (Praepagen(R)).

Sodium tripolyphosphate can be obtained from Rhodia, Paris, France. Zeolite can be obtained from Industrial Zeolite (UK) Ltd, Grays, Essex, UK. Citric acid and sodium citrate can be obtained from Jungbunzlauer, Basel, Switzerland. NOBS is sodium nonanoyloxybenzenesulfonate, supplied by Eastman, Batesville, Ark., USA.

TAED is tetraacetylethylenediamine, supplied under the Peractive(R) brand name by Clariant GmbH, Sulzbach, Germany.

Sodium carbonate and sodium bicarbonate can be obtained from Solvay, Brussels, Belgium.

Polyacrylate, polyacrylate/maleate copolymers can be obtained from BASF, Ludwigshafen, Germany.

Repel-O-Tex(R) can be obtained from Rhodia, Paris, France.

Texcare(R) can be obtained from Clariant, Sulzbach, Germany. Sodium percarbonate and sodium carbonate can be obtained from Solvay, Houston, Tex., USA.

Na salt of Ethylenediamine-N,N'-disuccinic acid, (S,S) isomer (EDDS) was supplied by Octel, Ellesmere Port, UK.

Hydroxy ethane di phosphonate (HEDP) was supplied by Dow Chemical, Midland, Mich., USA.

Enzymes Savinase(R), Savinase(R) Ultra, Stainzyme(R) Plus, Lipex(R), Lipolex(R), Lipoclean(R), Celluclean(R), Carezyme(R), Natalase(R), Stainzyme(R), Stainzyme(R) Plus, Termamyl(R), Termamyl(R) ultra, and Mannaway(R) can be obtained from Novozymes, Bagsvaerd, Denmark.

Enzymes Purafect(R), FN3, FN4 and Optisize can be obtained from Genencor International Inc., Palo Alto, Calif., US.

Direct violet 9 and 99 can be obtained from BASF DE, Ludwigshafen, Germany. Solvent violet 13 can be obtained from Ningbo Lixing Chemical Co., Ltd. Ningbo, Zhejiang, China. Brighteners can be obtained from Ciba Specialty Chemicals, Basel, Switzerland.

All percentages and ratios are calculated by weight unless otherwise indicated. All percentages and ratios are calculated based on the total composition unless otherwise indicated. It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Wash Assays

Launder-O-Meter (LOM) Model Wash System

The Launder-O-Meter (LOM) is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines.

Mini Launder-O-Meter (MiniLOM) Model Wash System

MiniLOM is a modified mini wash system of the Launder-O-Meter (LOM), which is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines.

In miniLOM, washes are performed in 50 ml test tubes placed in Stuart rotator.

Terg-O-Timeter (TOM) Wash Assay

The Tergo-To-Meter (TOM) is a medium scale model wash system that can be applied to test 12 different wash conditions simultaneously. A TOM is basically a large temperature controlled water bath with up to 12 open metal beakers submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the TOM beakers have no lid, it is possible to withdraw samples during a TOM experiment and assay for information on-line during wash.

The TOM model wash system is mainly used in medium scale testing of detergents and enzymes at US or LA/AP wash conditions. In a TOM experiment, factors such as the ballast to soil ratio and the fabric to wash liquor ratio can be varied. Therefore, the TOM provides the link between small scale experiments, such as AMSA and mini-wash, and the more time consuming full scale experiments in top loader washing machines.

Equipment: The water bath with 12 steel beakers and 1 rotating arm per beaker with capacity of 500 or 1200 mL of detergent solution. Temperature ranges from 5 to 80° C. The water bath has to be filled up with deionised water. Rotational speed can be set up to 70 to 120 rpm/min.

Set temperature in the Terg-O-Tometer and start the rotation in the water bath. Wait for the temperature to adjust (tolerance is +/−0.5° C.). All beakers shall be clean and without traces of prior test material.

The wash solution with desired amount of detergent, temperature and water hardness is prepared in a bucket. The detergent is allowed to dissolve during magnet stirring for 10 min. Wash solution shall be used within 30 to 60 min after preparation.

800 ml wash solution is added into a TOM beaker. The wash solution is agitated at 120 rpm and optionally one or more enzymes are added to the beaker. The swatches are sprinkled into the beaker and then the ballast load. Time measurement starts when the swatches and ballast are added to the beaker. The swatches are washed for 20 minutes after which agitation is terminated. The wash load is subsequently transferred from the TOM beaker to a sieve and rinse with cold tap water. The soiled swatches are separated from the ballast load. The soil swatches are transferred to a 5 L beaker with cold tap water under running water for 5 minutes. The ballast load is kept separately for the coming inactivation. The water is gently pressed out of the swatches by hand and placed on a tray covered with a paper. Another paper is placed on top of the swatches. The swatches are allowed to dry overnight before subjecting the swatches to analysis, such as measuring the color intensity using a Color Eye as described herein.

Enzyme Assays

Assay I: Testing of DNase Activity

DNase activity was determined on DNase Test Agar with Methyl Green (BD, Franklin Lakes, N.J., USA), which was prepared according to the manual from supplier. Briefly, 21 g of agar was dissolved in 500 ml water and then autoclaved for 15 min at 121° C. Autoclaved agar was temperated to 48° C. in water bath, and 20 ml of agar was poured into petridishes with and allowed to solidify by incubation o/n at room temperature. On solidified agar plates, 5 µl of enzyme solutions are added and DNase activity is observed as colorless zones around the spotted enzyme solutions.

Assay II

Analysis of E-2-nonenal on textile using an electronic nose.

One way of testing for the presence of malodor on textiles is by using E-2-Nonenal as a marker for the malodor, as this compound contributes to the malodor on laundry.

Add a solution of E-2-nonenal to a 5 cm×5 cm textile swatch and place the swatch in a 20 mL glass vial for GC analysis and cap the vial. Analyze 5 mL headspace from the capped vials in a Heracles II Electronic nose from Alpha M.O.S., France (double column gas chromatograph with 2 FIDs, column 1: MXTS and column 2: MXT1701) after 20 minutes incubation at 40° C.

EXAMPLES

Methods

General methods of PCR, cloning, ligation nucleotides etc. are well-known to a person skilled in the art and may for example be found in in "Molecular cloning: A laboratory manual", Sambrook et al. (1989), Cold Spring Harbor lab., Cold Spring Harbor, N.Y.; Ausubel, F. M. et al. (eds.); "Current protocols in Molecular Biology", John Wiley and Sons, (1995); Harwood, C. R., and Cutting, S. M. (eds.); "DNA Cloning: A Practical Approach, Volumes I and II", D. N. Glover ed. (1985); "Oligonucleotide Synthesis", M. J. Gait ed. (1984); "Nucleic Acid Hybridization", B. D. Hames & S. J. Higgins eds (1985); "A Practical Guide To Molecular Cloning", B. Perbal, (1984).

Example 1

Cloning and Expression of Bacterial DNases

The DNases were derived from bacterial strains isolated from environmental samples by standard microbiological isolation techniques or by metagenomic sequencing of DNA isolated from environmental samples. Pure strains were identified and taxonomy was assigned based on DNA sequencing of the 16S ribosomal genes (Table 1).

TABLE 1

| Organism | Source Country | SEQ ID: |
| --- | --- | --- |
| Paenibacillus sp-62212 | Sweden | 1 |
| Paenibacillus sp-62605 | Sweden | 2 |
| Bacillus sp-62738 | Denmark | 3 |
| Bacillus pumilus | United states | 4 |
| Bacillus horikoshii | Japan | 5 |
| Bacillus sp-62490 | United states | 6 |
| Bacillus sp-13390 | Greece | 7 |

TABLE 1-continued

| Organism | Source Country | SEQ ID: |
| --- | --- | --- |
| Jeotgalibacillus sp-13376 | Canada | 8 |
| Bacillus sp-62738 | Denmark | 9 |
| Streptomyces iakyrus | Jamaica | 10 |
| Streptococcus infantis | Sweden | 11 |
| Bacillus sp-62599 | Sweden | 12 |
| Bacillus akibai | Greece | 13 |
| Paenibacillus xylanexedens | Denmark | 14 |
| Fictibacillus sp-62719 | United states | 15 |
| Bacillus algicola | Denmark | 16 |
| Exiguobacterium sp. NG55 | United states | 17 |
| Metagenome from environmental sample J | United states | 18 |
| Streptomyces thermoalcalitolerans (D5M41741) | Indonesia | 19 |
| Metagenome of environmental sample C | Spain | 20 |

Chromosomal DNA was isolated from pure cultures of the individual strains or from mixed environmental cultures with the DNeasy Blood & Tissue Kit from Qiagen (Hilden, Germany) and subjected to full genome sequencing using Illumina technology. Genome sequencing, the subsequent assembly of reads and the gene discovery (i.e. annotation of gene functions) is known to the person skilled in the art and the service can be purchased commercially.

The genome sequences were analyzed for putative DNases from the PFAM database families PF14040, PF07510, PF01223 and PF00565 (R. D. Finn et al. Nucleic Acids Research (2014), 42:D222-D230). This analysis identified twenty genes encoding putative DNases which were subsequently cloned and recombinantly expressed in Bacillus subtilis.

The genes encoding the DNases were amplified by PCR or chemically synthesized and fused with regulatory elements, affinity purification tag and homology regions for recombination into the B. subtilis genome. The linear integration construct was a SOE-PCR fusion product (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68) made by fusion of the gene between two Bacillus subtilis chromosomal regions along with strong promoters and a chloramphenicol resistance marker. The SOE PCR method is also described in patent application WO 2003095658. The genes were expressed under the control of a triple promoter system (as described in WO 99/43835), consisting of the promoters from Bacillus licheniformis alpha-amylase gene (amyL), Bacillus amyloliquefaciens alpha-amylase gene (amyQ), and the Bacillus thuringiensis cryIIIA promoter including stabilizing sequence. The genes were fused with DNA encoding a Bacillus clausii secretion signal (encoding the following amino acid sequence: MKKPLGKIVASTALLISVAFSSSIASA (SEQ ID NO 21)) replacing the native secretion signal. Furthermore the expression construct results in the addition of a carboxy-terminal poly histidine tail consisting of 6 consecutive histidine residues. The SOE-PCR products were transformed into Bacillus subtilis and integrated in the chromosome by homologous recombination into the pectate lyase locus. Subsequently a recombinant Bacillus subtilis clone containing the integrated expression construct was grown in liquid culture. The culture broth was centrifuged (20000×g, 20 min) and the supernatant was carefully decanted from the precipitate and used for purification of the enzyme or alternatively sterile filtered supernatant was used directly for assays.

Example 2

MiniLOM Liquid Detergent

Isolating Laundry Specific Bacterial Strains

One strain of *Brevundimonas* sp. isolated from laundry was used in the present example. The *Brevundimonas* sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Color was used, whereas WFK IEC-A* model detergent was used for washing at 60° C. Ariel Sensitive White & Color was prepared by weighing out 5.1 g and adding tap water up to 1000 ml followed by stirring for 5 minutes. WFK IEC-A* model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C.

Laundry was sampled immediately after washing at 15, 40 and 60° C., respectively. Twenty grams of laundry was added 0.9% (w/v) NaCl (1.06404; Merck, Damstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Swatches with Biofilm

*Brevundimonas* sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, *Brevundimonas* sp. was pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an $OD_{600\ nm}$ of 0.03, and 1.6 mL was added into each well of a 12-well polystyrene flat-bottom microplate (3512; Corning Incorporated, Corning, N.Y., USA), in which a round swatch (diameter 2 cm) of sterile Polyester WFK30A was placed. After incubation (24 h at 15° C. with shaking (100 rpm), swatches were rinsed twice with 0.9% (w/v) NaCl.

Wash Experiment

Wash liquor of liquid model detergent A were prepared by weighing out and dissolving detergent in water with water with hardness 15° dH. Dosing of model detergent A was 3.33 g/L. Pigment soil (Pigmentschmutz, 09V, wfk, Krefeld, Germany) (0.7 g/L) was added to the wash liquor. DNases (0.5 ppm) was added to the wash liquor. As control, wash liquor without DNases was made. Wash liquor (10 ml) was added to a 50 ml test tube, in which five rinsed swatches with *Brevundimonas* sp. biofilm and five sterile polyester (WFK30A) swatches were placed. Test tubes were placed in a Stuart rotator (Mini LOM) for 1 hour at 30° C. Swatches were rinsed twice with tap water and dried on filter paper over night. Color difference (L values) was measured using a Color Eye (Macbeth Color Eye 7000 reflectance spectrophotometer). The measurements were made without UV in the incident light and the L value from the CIE Lab color space was extracted. The color difference (L value, L*) represents the darkest black at L*=0, and the brightest white at L*=100. Data is represented as Delta L values meaning the L value of the swatch washed with DNases minus the L value of swatch washed without DNases.

TABLE 2

Deep cleaning effect of the DNases

| Host name | L-value Model detergent A | ΔL Model detergent A |
|---|---|---|
| No enzyme | 83.59 | n/a |
| *Paenibacillus* sp-62212 | 84.34 | 0.76 |
| *Paenibacillus* sp-62605 | 87.68 | 4.09 |
| *Bacillus* sp-62738 | 85.46 | 1.88 |
| *Bacillus pumilus* | 84.18 | 0.60 |
| *Bacillus horikoshii* | 88.11 | 4.52 |
| *Bacillus* sp-62490 | 84.61 | 1.03 |
| *Bacillus* sp-13390 | 87.16 | 3.57 |
| *Jeotgalibacillus* sp-13376 | 88.80 | 5.21 |
| *Bacillus* sp-62738 | 84.78 | 1.20 |
| *Streptomyces iakyrus* | 88.17 | 4.58 |
| *Streptococcus infantis* | 87.93 | 4.35 |
| *Bacillus* sp-62599 | 88.32 | 4.73 |
| *Bacillus akibai* | 86.04 | 2.45 |
| *Paenibacillus xylanexedens* | 85.25 | 1.67 |
| *Penicillium reticulisporum* | 88.00 | 4.41 |
| *Fictibacillus* sp-62719 | 92.93 | 3.66 |
| *Bacillus algicola* | 92.82 | 3.55 |
| *Exiguobacterium* sp. NG55 | 91.69 | 2.42 |
| Metagenome from environmental sample J | 93.11 | 3.84 |
| *Streptomyces thermoalcalitolerans* | 90.31 | 1.04 |
| Metagenome from environmental sample C | 90.65 | 1.38 |

Tables 2 show that all the tested DNases have "deep cleaning" effect i.e. reduce or remove the biofilm or components of the biofilm swatches in a liquid detergent.

The invention claimed is:

1. A detergent composition comprising a polypeptide having DNase activity and an effective amount of a surfactant to improve wash performance of the detergent composition as compared to the same detergent composition without the effective amount of the surfactant, wherein
the amino acid sequence of the polypeptide having DNase activity has at least 90% sequence identity to the amino acid sequence of SEQ ID NO: 1,
the composition is a bar, a homogenous tablet, a tablet having two or more layers, a pouch having one or more compartments, a regular or compact powder, a granule, a paste, a gel, or a regular, compact or concentrated liquid, and
wherein the detergent composition reduces soil deposition onto a Brevundiomonas biofilm swatch in a wash assay as compared to the amount of soil deposition by the same detergent composition without said polypeptide having DNase activity.

2. The detergent composition of claim 1, wherein the amino acid sequence of the polypeptide having DNase activity has at least 95% sequence identity to the amino acid sequence of SEQ ID NO: 1.

3. The detergent composition of claim 1, wherein the amino acid sequence of the polypeptide having DNase activity has at least 97% sequence identity to the amino acid sequence of SEQ ID NO: 1.

4. The detergent composition of claim 1, wherein the amino acid sequence of the polypeptide having DNase activity comprises the amino acid sequence of SEQ ID NO: 1.

5. The detergent composition of claim 1, wherein the polypeptide having DNase activity is a variant of the amino acid sequence of SEQ ID NO: 1, wherein the amino acid sequence of the variant comprises a substitution, deletion, and/or insertion at one or more positions relative to the amino acid sequence of SEQ ID NO: 1.

6. The detergent composition of claim 1, wherein the polypeptide having DNase activity is a fragment of the amino acid sequence of SEQ ID NO: 1, wherein the fragment has DNase activity.

7. The detergent composition of claim 1, further comprising a detergent adjunct ingredient selected from the group consisting of builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders, cobuilders, fabric huing agents, anti-foaming agents, dispersants, processing aids, and pigments.

8. The detergent composition of claim 1, further comprising one or more enzymes selected from the group consisting of amylases, arabinases, carbohydrases, cellulases, cutinases, galactanases, lipases, mannanases, oxidases, pectinases, proteases, and xylanases.

9. The detergent composition of claim 8, wherein the one or more enzymes comprises a protease.

10. The detergent composition of claim 9, wherein the protease is a serine protease.

11. A method for laundering a textile, comprising:
(a) exposing the textile to a wash liquor comprising the detergent composition of claim 1; and
(b) completing at least one wash cycle.

12. The method of claim 11, further comprising rinsing the textile.

13. The method of claim 11, wherein the concentration of the polypeptide having DNase activity in the wash liquor is at least 1 mg per liter of wash liquor.

14. The method of claim 11, wherein the pH of the wash liquor is in the range 5.5 to 11.

15. The method of claim 11, wherein the temperature of the wash liquor is in the range of 5 to 95° C.

16. The method of claim 11, wherein the textile is made of cotton, polyacryl, polyamide, polyester, and/or silk.

17. The method of claim 11, further comprising a second wash cycle.

18. The detergent composition of claim 1, wherein the detergent composition is a regular, compact or concentrated liquid, and wherein the surfactant is present in an amount of 2 wt % to 60 wt % of the detergent composition.

19. The detergent composition of claim 1, wherein the detergent composition is a granule comprising 5 wt % to 50 wt % anionic surfactant and 1 wt % to 8 wt % nonionic surfactant.

20. The detergent composition of claim 1, wherein the surfactant is selected from the group consisting of alkyl ether sulphates, C9-C15 alcohol ethersulfates, C12-C15 primary alcohol ethoxylate, C8-C16 ester sulphates and C10-C14 ester sulphates, mono dodecyl ester sulphates, sulfates, sulfonates, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates, disulfonates, alkyl sulfates (AS), sodium dodecyl sulfate (SDS), fatty alcohol sulfates (FAS), primary alcohol sulfates (PAS), alcohol ethersulfates (AEOS), secondary alkanesulfonates (SAS), paraffin sulfonates (PS), ester sulfonates, sulfonated fatty acid glycerol esters, alpha-sulfo fatty acid methyl esters, methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

21. The detergent composition of claim 1, wherein the surfactant is LAS or AEOS, and wherein the surfactant is present in an amount of 1% to 15% of the detergent composition.

* * * * *

UNITED STATES PATENT AND TRADEMARK OFFICE
CERTIFICATE OF CORRECTION

| | |
|---|---|
| PATENT NO. | : 10,844,360 B2 |
| APPLICATION NO. | : 15/737169 |
| DATED | : November 24, 2020 |
| INVENTOR(S) | : Gjermansen et al. |

It is certified that error appears in the above-identified patent and that said Letters Patent is hereby corrected as shown below:

On the Title Page

Item (30) "Foreign Application Priority Data", please insert:
-- Oct 7, 2015 (DK) ......................2015 00615
Oct 7, 2015 (DK)........................2015 00618 --.

Item (56) "Foreign Patent Document", please delete:
"WO 01/986214"
And insert:
-- WO 01/98214 --.

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*